(12) United States Patent
Xu et al.

(10) Patent No.: US 7,118,990 B1
(45) Date of Patent: Oct. 10, 2006

(54) METHODS FOR MAKING LARGE DIMENSION, FLEXIBLE PIEZOELECTRIC CERAMIC TAPES

(75) Inventors: Baomin Xu, Cupertino, CA (US); Steven A. Buhler, Sunnyvale, CA (US); William S. Wong, San Carlos, CA (US); Michael C. Weisberg, Woodside, CA (US); Scott E. Solberg, Mountain View, CA (US); Karl A. Littau, Palo Alto, CA (US); Scott A. Elrod, La Honda, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 37 days.

(21) Appl. No.: 11/017,470

(22) Filed: Dec. 20, 2004

Related U.S. Application Data

(62) Division of application No. 10/376,527, filed on Feb. 25, 2003, now Pat. No. 6,964,201.

(51) Int. Cl.
*H01L 21/30* (2006.01)
*H01L 21/46* (2006.01)

(52) U.S. Cl. .................. 438/455; 438/405; 438/458

(58) Field of Classification Search ............ 438/405, 438/406, 455, 456, 458, 459
See application file for complete search history.

(56) References Cited

U.S. PATENT DOCUMENTS

| | | | |
|---|---|---|---|
| 4,233,477 A | 11/1980 | Rice et al. | |
| 4,237,399 A | 12/1980 | Sakamoto | |
| 4,670,682 A | 6/1987 | Harnden, Jr. et al. | |
| 4,991,283 A | 2/1991 | Johnson et al. | |
| 5,248,912 A | 9/1993 | Zdeblick et al. | |
| 5,430,344 A | 7/1995 | Takeuchi et al. | |
| 5,486,494 A | 1/1996 | Hotchkiss et al. | |
| 5,585,136 A | 12/1996 | Barrow et al. | |
| 5,691,593 A | 11/1997 | Takeuchi et al. | |
| 5,869,189 A | 2/1999 | Hagood, IV et al. | |

(Continued)

FOREIGN PATENT DOCUMENTS

JP    63150979 A    6/1988

(Continued)

OTHER PUBLICATIONS

Barrow, et al., *Characterization of Thick Lead Zirconate Titanate Films Fabricated Using a New Sol Gel Based Process;* J. Appl. Phys. 81 (2), Jan. 15, 1997, 1997 American Institute of Physics, pp. 876-881.

(Continued)

*Primary Examiner*—Phuc T. Dang
(74) *Attorney, Agent, or Firm*—Fay, Sharpe, Fagan, Minnich & McKee, LLP

(57) ABSTRACT

A method for producing a detection/test tape includes depositing a material onto a surface of at least one first substrate to form a plurality of element structures. Electrodes are deposited on a surface of each of the plurality of element structures, and the element structures are bonded to a second substrate, where the second substrate is conductive or has a conductive layer, and the second substrate is carried on a carrier plate. The at least one first substrate is removed from the element structures and second side electrodes are deposited on a second surface of each of the plurality of element structures. An insulative material is inserted around the element structures to electrically isolate the two substrates used to bond the element structures. A second side of the element structures is then bonded to another substrate, where the other substrate is conductive or has a conductive layer. Thereafter, the carrier plate carrying the second substrate is removed.

19 Claims, 16 Drawing Sheets

U.S. PATENT DOCUMENTS

| | | | |
|---|---|---|---|
| 5,950,291 | A | 9/1999 | Gentilman et al. |
| 6,071,795 | A | 6/2000 | Cheung et al. |
| 6,262,516 | B1 | 7/2001 | Fukuda et al. |
| 6,335,263 | B1 | 1/2002 | Cheung et al. |
| 6,370,964 | B1 | 4/2002 | Chang et al. |
| 6,408,513 | B1 | 6/2002 | Kitahara et al. |
| 6,476,540 | B1 | 11/2002 | Takeuchi et al. |
| 6,645,830 | B1 | 11/2003 | Shimoda et al. |
| 6,666,943 | B1 | 12/2003 | Wada et al. |
| 6,715,192 | B1 | 4/2004 | Takeuchi et al. |
| 6,771,007 | B1 | 8/2004 | Tanielian |
| 2002/0036055 | A1* | 3/2002 | Yoshimura et al. ......... 156/234 |
| 2002/0149296 | A1 | 10/2002 | Fujii et al. |

FOREIGN PATENT DOCUMENTS

| | | |
|---|---|---|
| JP | 02005325 A | 1/1990 |
| JP | 04023370 A | 1/1990 |
| JP | 02162782 A | 6/1990 |
| WO | WO 99/48621 A | 9/1999 |
| WO | WO 01/39253 A | 5/2001 |

OTHER PUBLICATIONS

Wong, W.S., et al., *Integration of GaN Thin Films with Dissimilar Substrate Materials by Pd-In Metal Bonding and Laser Lift-Off*; Journal of Electronic Materials, vol. 28, No. 12, 1999, pp. 1409-1413.

Chen, Yi-Chia, et al., *A Fluxless Bonding Technology Using Indium-Silver Multilayer Composites*; IEEE Transactions on Components, Packaging, and Manufacturing Technology—Part A., vol. 20, No. 1, Mar. 1997, pp. 46-51.

Lee, Chin C., et al., *Au-In Bonding Below the Eutectic Temperature*; IEEE Transactions on Components, Hybrids, and Manufacturing Technology, vol. 16, No. 3, May 1998, pp. 311-316.

Chen, Yi-Chia, *Indium-Copper Multilayer Composites for Fluxless Oxidation-Free Bonding*; Thin Solid Films 283 (1996), pp. 243-246; 1996 Elsevier Science S.A.

Mathelin, D., et al., *Improved Microcontact Technology*, The Compete Network presents Immico, (BE-8225), Up-dated: Spring 1998, pp. 1-9.

Sayer, M., et al., *Macroscopic Actuators Using Thick Piezoelectric Coatings;* Mat. Res. Soc. Symp. Proc., vol. 655, 2001 Materials Research Society; pp. CC13.6.1-CC13.6.11.

Lin, Mark, et al., *The Manufacture of Composite Structures with a Built-in Network of Piezoceramics*; Composites Science and Technology, 62 (2002), pp. 919-939.

Zou, L. et al., *Sol-Gel Fabricated Thick Piezoelectric Ultrasonic Transducers for Potential Applications in Industrial Material Processes*; 1997 IEEE Ultrasonics Symposium, pp. 1007-1011.

Qi, Wenkang et al., "Finite Element Study on Random Design of 2-2 Composite Transducer", Proceedings of SPIE—The International Society for Optical Engineering 1997 Society of Photo-Optical Instrumentation Engineers, Bellingham, WA, US, vol. 3037, 1997, pp. 176-180.

Sundaresan, M.J. et al., "Methods of Distributed Sensing for Health Monitoring of Composite Material Structures", Composites Part A: Applied Science and Manufacturing, Elsevier Science Publishers B.V., Amsterdam, NL, vol. 32, No. 9, Sep. 2001, pp. 1357-1374.

European Search Report, Feb. 15, 2006, Application No. EP 04 004266.

Tressler, J.F. et al., "Functional Composites for Sensors, Actuators and Transducers", Composites Part A: Applied Science and Manufacturing, Elsevier Science Publishers B.V., Amsterdam, NL, vol. 30, No. 4, Apr. 1999, pp. 477-482.

Tsakalakos, L. et al., *Epitaxial Ferroelectric (Pb,La)(Zr Ti)$O_3$ Thin Films on Stainless Steel by Excimer Laser Liftoff*, Applied Physics Letters, Jan. 10, 2000, vol. 76, No. 2, pp. 227-229.

Tsakalakos, L. et al., *Excimer Laser Liftoff of Epitaxial Pr(Zr, Ti)$O_3$ Thin Films and Heterostructures*; Mat. Res. Soc. Symp. Proc., vol. 596, 2000 Materials Research Society, pp. 549-557; Ferroelectric Thin Films VIII, Nov. 29-Dec. 2, 1999.

Lukacs, M. et al., *Novel PZT Films for Ultrasound Biomicroscopy*; 1996 IEEE Ultrasonics Symposium, pp. 901-904.

\* cited by examiner

FIG. 3
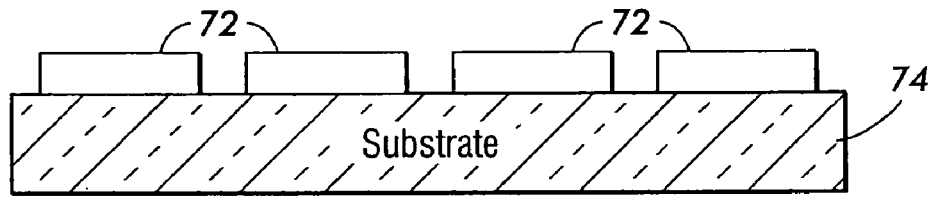
FIG. 4A
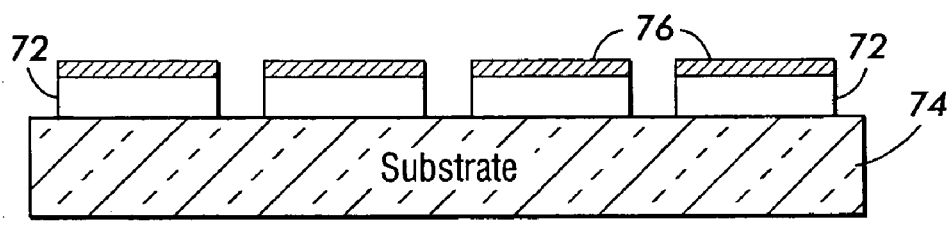
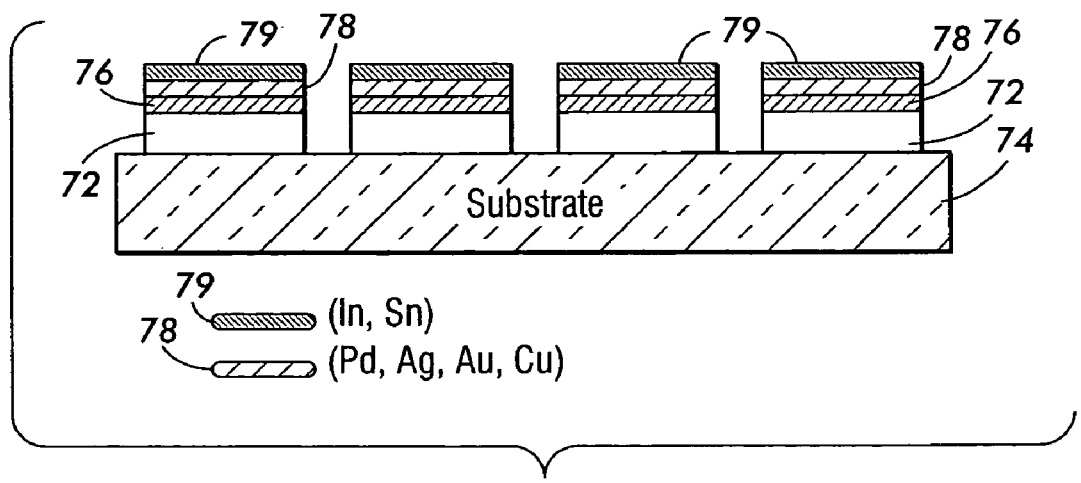
FIG. 4B

FIG. 19
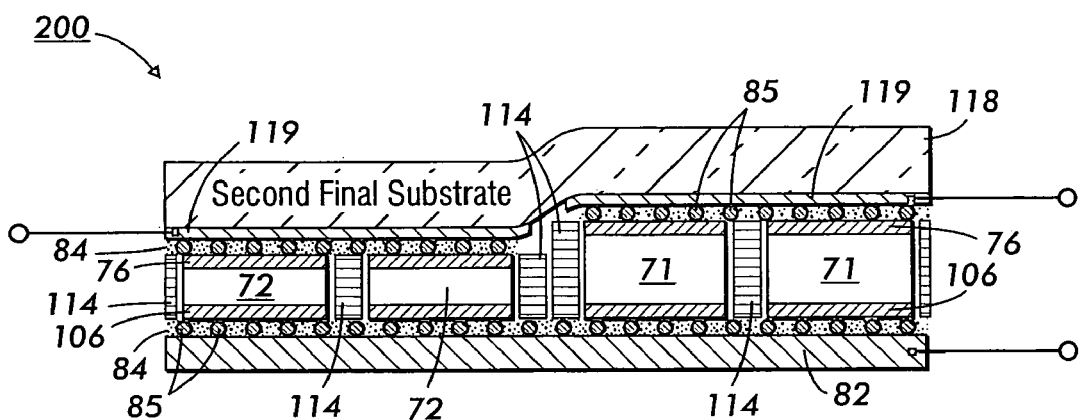
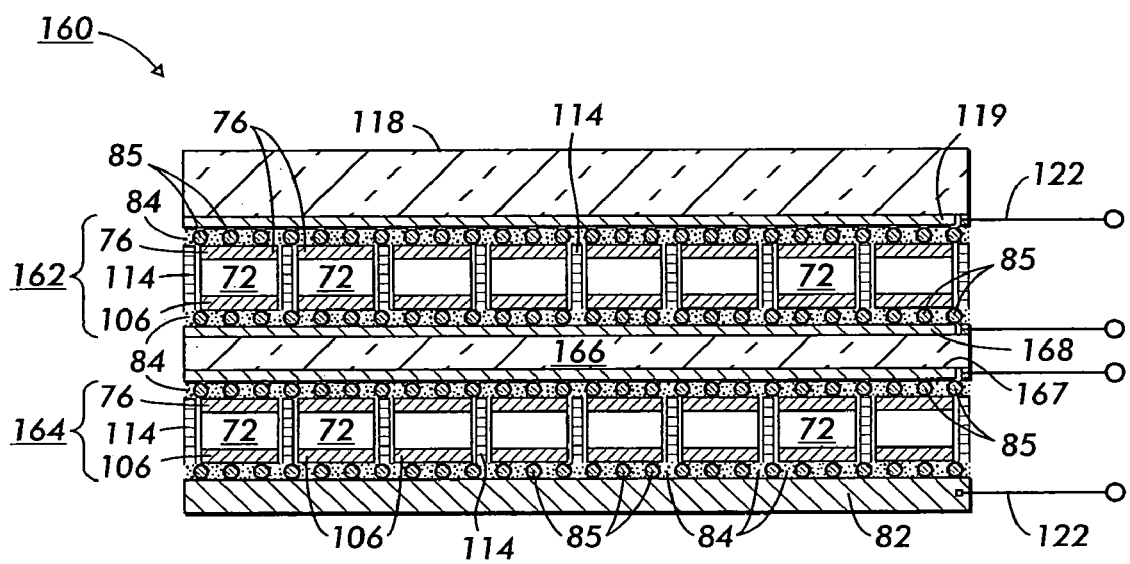
FIG. 20

METHODS FOR MAKING LARGE DIMENSION, FLEXIBLE PIEZOELECTRIC CERAMIC TAPES

This application is a Div of Ser. No. 10/376,527 filed Feb. 25, 2003 (U.S. Pat. No. 6,964,201)

BACKGROUND OF THE INVENTION

Piezoelectric ceramics are commonly being used as sensors, actuators and transducers because of their strong electromechanical coupling effect.

A detection/test system, which combines such sensors, actuators, transducers with feedback or feed-forward control circuitry, is an important technology for many industry and military applications. One particular application is the active control of vibrations. For example, active control of the vibration inside the body of an airplane can greatly reduce the noise in the passenger cabin. Active control of the vibration of the wings can greatly reduce the damping by airflow and thus increase the efficiency of the airplane. Relatedly, active control of the vibration of a submarine can greatly reduce the acoustic noise it generates and thus greatly reduce its chance of being detected. Another application of detection/test systems is real-time structural health monitoring. For example, embedded sensors and transducers in a structure can produce in-site detection of cracks in the structures and thus predict and assist in avoiding critical failure of the structure.

A significant drawback of piezoelectric ceramics is that it is difficult to make a thin, large sheet (at many inches to several feet scale), due to the brittle nature of the material. Due to this limitation, it cannot be mounted to a curved surface or embedded in a structure which needs to be flexible. Unfortunately, many real world applications require detecting and testing of curved surfaces and/or flexible structure, thus the mentioned brittleness greatly limits the applications of piezoelectric ceramic materials in detection/test systems.

An alternative is to use piezoelectric polymers which are flexible and can be manufactured in large scale. Unfortunately, the piezoelectric effect of piezoelectric polymers is weak—about one-tenth of piezoelectric ceramics—and the materials are very soft.

One path taken to develop a detector/test system is represented by research at Stanford University and which is coined as the Stanford Multi-Actuator-Receiver Transduction Layer (SMART layer). Particularly, a manufacturing method has been proposed for integrating a network of distributed piezoceramic actuators/sensors onto laminated carbon/epoxy composite structures. The network of built-in actuators/sensors is used to monitor the health of the host composite structure by acquiring information about the condition of the structure throughout its life. The manufacturing method applies a printed circuit board technique to fabricate a thin flexible layer with a network of piezoceramics. It is used as an extra ply that is either inserted into or bonded onto the surface of a composite laminate to give it actuating and sensing capabilities. More particularly, the system implements the use of a flexible printed circuit, commonly referred to as "Flex." The proposed concept used the Flex technique to make a large, thin flexible layer that contains a network of distributed piezoceramics connected by printed circuits.

However, the fabrication techniques for the SMART layer are labor intensive and restrictive in design choices. Particularly, the disclosed fabrication process for the SMART layer do not lend itself to obtaining of a flexible tape with high density elements and a variety of geometric shapes for those elements, which in turn permits more versatile functional capabilities. It also does not consider use of elements within a thickness range of about 10 µm, or greater, formed by a direct marking technology.

SUMMARY OF THE INVENTION

A flexible detection/test tape includes a first flexible conductive layer, and a second flexible conductive layer positioned opposite the first conductive layer. A plurality of at least one of sensors, actuators or transducers are positioned between and are bonded to the first flexible conductive layer and the second flexible conductive layer. An insulative material is inserted around the plurality of at least one of the sensors, actuators or transducers. An electrical contact network connects to the first flexible conductive layer and the second flexible conductive layer, whereby power and control signals are provided to the flexible detection test tape.

In an alternative embodiment, a method for producing a detection/test tape includes depositing a material onto a surface of a first substrate to form a plurality of element structures. Electrodes are deposited on a surface of each of the plurality of element structures, and the element structures are bonded to a second substrate, where the second substrate is conductive or has a conductive layer, and the second substrate is carried on a carrier plate. The first substrate is removed from the element structures and second side electrodes are deposited on a second surface of each of the plurality of element structures. An insulative material is inserted around the element structures to electrically isolate the two substrates used to bond the element structures. A second side of the element structures is then bonded to another substrate, where the other substrate is conductive or has a conductive layer. Thereafter, the carrier plate carrying the second substrate is removed.

SUMMARY OF THE DRAWINGS

The invention may take form in various components and arrangements of components, and in various steps and arrangements of steps. The drawings are only for purposes of illustrating preferred embodiments and are not to be construed as limiting the invention.

FIG. 3 illustrates a piezoelectric element array on a top surface of a carrier substrate;

FIGS. 4A and 4B show alternative embodiments of a piezoelectric element array deposited with electrodes and other thin film metals for bonding, the piezoelectric element array is on a top surface of a carrier substrate;

FIG. 19 is yet a further cross section view for one embodiment of a completed piezoelectric tape according to the present application;

FIG. 20 is a two-layer piezoelectric tape which may be accomplished in accordance with the concepts of the present application.

DETAILED DESCRIPTION OF THE INVENTION

The present application provides for flexible detection/test tape and processes to make such a tape. In one design, a plurality of piezoelectric ceramic elements are sandwiched between two conductive layers, such as two metallized polymer films or tapes, two metal foils, or one metallized polymer tape and one metal foil. The configuration provides the assemblied piezoelectric tape with flexibility and a potential dimension of several feet or more in scale. As will be described in greater detail, the metallization layer in the polymer film can be patterned in such ways that the piezoelectric elements can be connected to external circuitry as individual elements, as several groups, of elements, or as a single group. Thus the piezoelectric tape can work simultaneously as sensors, actuators or transducers. The area density and the shape of the piezoelectric elements can be varied locally to meet the application requirements. Also, since the disclosed manufacturing process permits for a high density of elements, the operational functionality of the tape will not be significantly less than a sheet of piezoelectric elements. The piezoelectric ceramic tapes can be made by a process which combines screen printing or other direct marking method, high temperature sintering, tape polishing, laser or other radiation liftoff, a thin layer bonding which can remain electric contact between the bonded parts. Specifics of the process will now be described.

Figure 1:
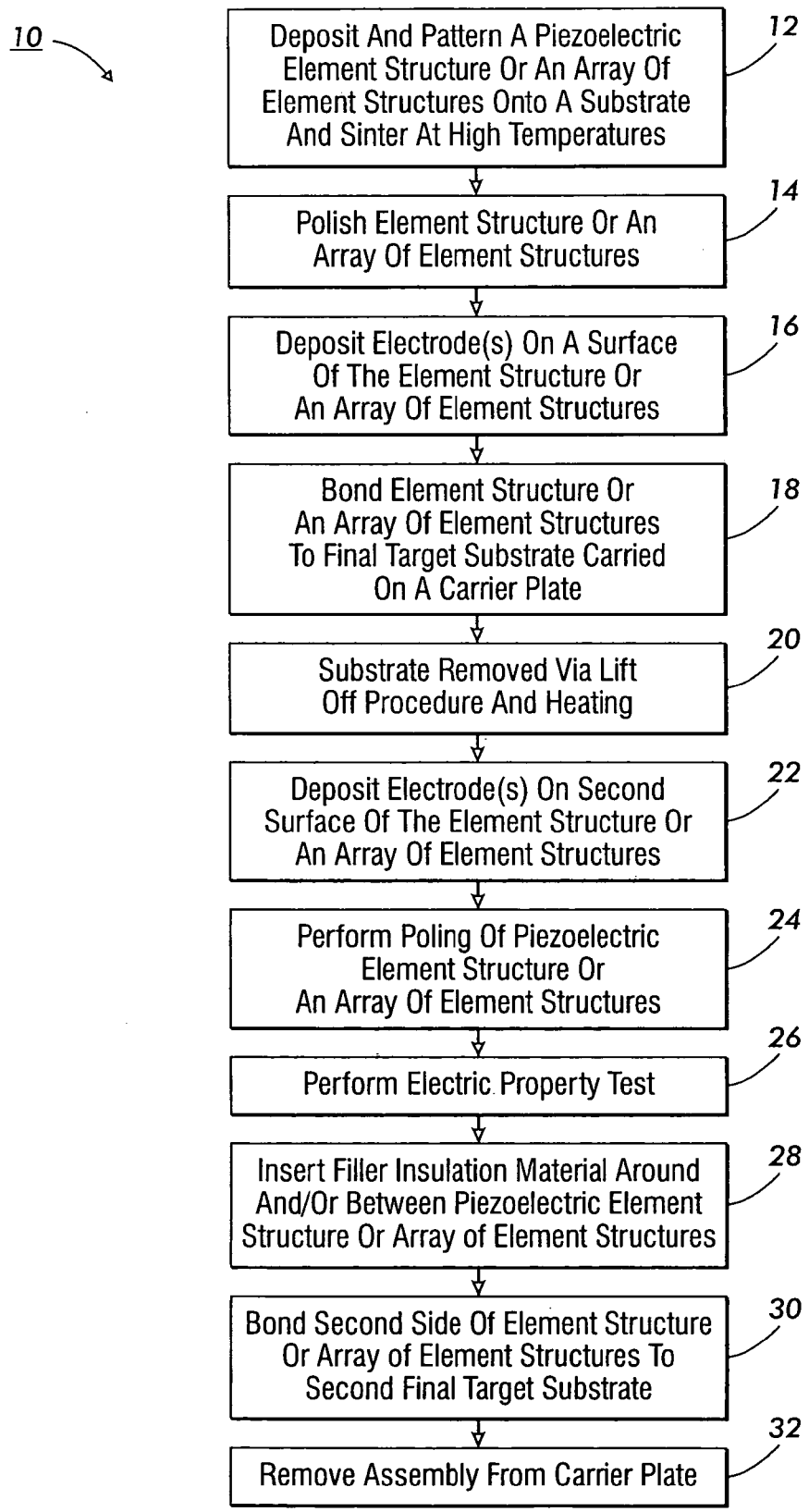
FIG. 1 is a high level process flow for piezoelectric detection/test tape production.

FIG. 1 illustrates a high level process flow 10 for a first embodiment of a manufacturing process according to the concepts of the present application. While the following discussion focuses on producing piezoelectric thick film elements (with thickness between 10 and 100 µm), it is to be appreciated the disclosed processes may be used with other materials and may also be used for production of thin-film elements (with thickness less than 10 µm) and elements with thicknesses greater than 100 µm to millimeter in scale. Also, the following techniques are intended to be applicable to the generation of individual elements and arrays of elements.

Initially, piezoelectric ceramic thick film elements are fabricated by depositing the piezoelectric material onto an appropriate substrate by use of a direct marking technology 12. In the deposition techniques employed, ceramic type powders are used in a preferred embodiment. The fabrication process includes sintering the material preferably at a temperature of approximately 1100 to 1350° C. for densification, although other temperature ranges may also be used in appropriate circumstances. Following the fabrication process the surface of the formed structures of piezoelectric elements are polished 14, preferably using a dry tape polishing technique. Once the piezoelectric elements have been polished and cleaned, electrodes are deposited on the surface of the piezoelectric elements 16. Next, the piezoelectric elements are permanently bonded to a final target substrate 18. The final target substrate is flexible and conductive or has a surface conductive layer, such as a metal foil or a metallized polymer tape. In order to easily carry during the fabrication process, the flexible target substrate can be put on another rigid carrier plate. Typically, the composition of the piezoelectric ceramic elements is doped or undoped PZT (lead zirconate titanate), but any other piezoelectric materials, such as lead titanate, lead zirconate, lead magnesium titanate and its solid solutions with lead titanate, lithium niobate, lithium tantanate, and others may be used.

At this point, the substrate on which the piezoelectric elements were deposited is removed through a liftoff process using radiation energy such as from a laser or other appropriate device 20. The releasing process involves exposure of the piezoelectric elements to a radiation source through the substrate, to break an attachment interface between the substrate and the piezoelectric elements. Additional heating is implemented, if necessary, to complete removal of the substrate. Once the liftoff process has been completed, a second electrode is deposited on a second surface of the piezoelectric material 22. Thereafter, poling of the elements under high voltage obtains piezoelectric properties in the material 24. The electric property, for example, a dielectric property, of each element is then measured 26 to identify if the elements meet required criteria. An insulative filler is inserted between the piezoelectric elements 28, whereafter the piezoelectric elements are bonded to the second final target substrate 30. Again the second final target substrate is flexible, such as a metal foil or metallized polymer tape. The assembled arrangement can then be removed from the carrier plate 32.

Figure 2:
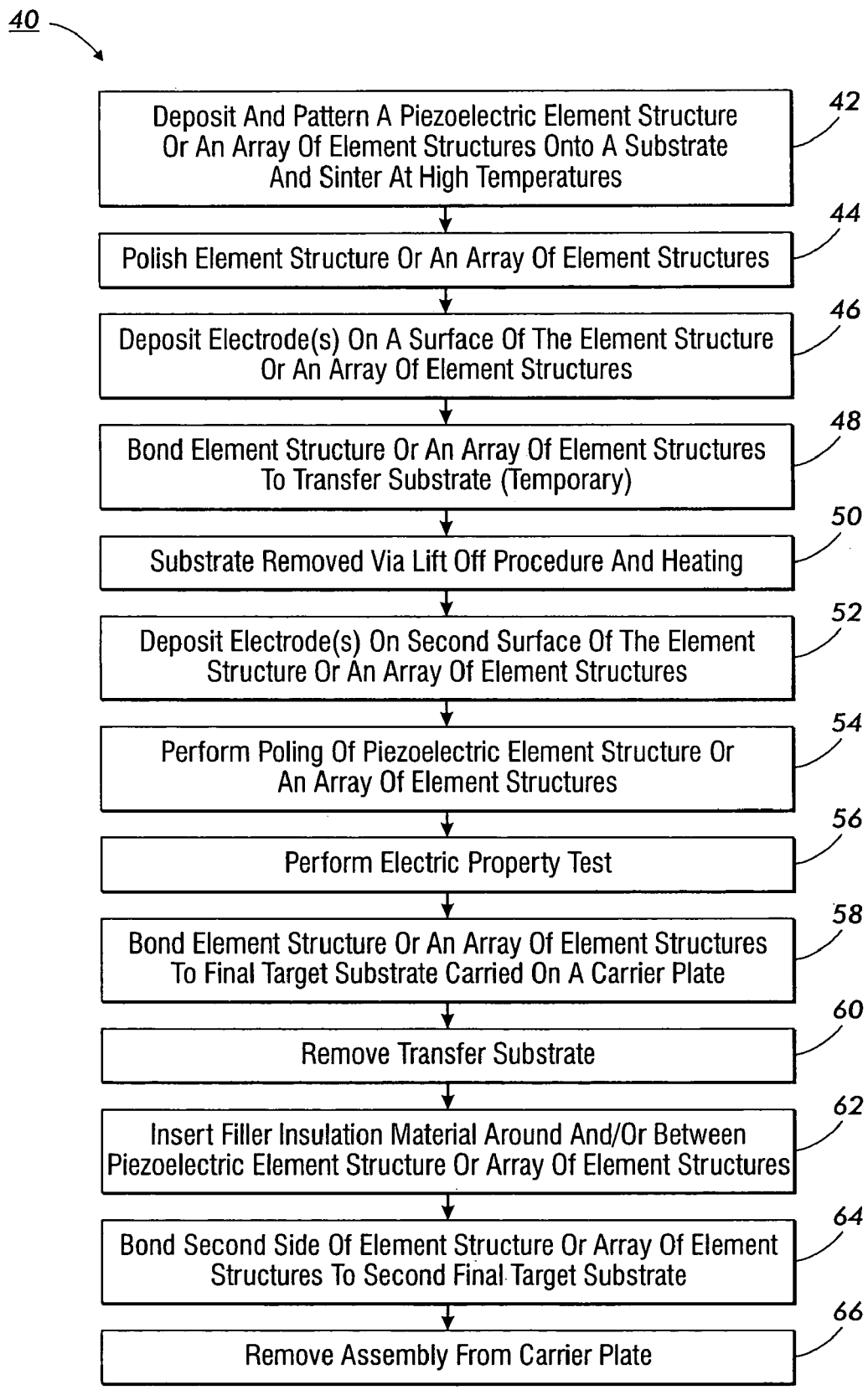
FIG. 2 is a high level process flow for piezoelectric detection/test tape production including attachment of the piezoelectric elements to a transfer substrate prior to completion of the tape production process.

Turning to FIG. 2, illustrated is a second high-level process flow 40 for a second embodiment of the present application. This process differs from FIG. 1 in that the bonding is to a transfer substrate rather than to a final target substrate. Thus, the fabrication step 42, the tape polishing step 44 and the electrode depositing step 46 are performed in the same manner as steps 12, 14 and 16 of FIG. 1. At bonding step 48, the bonding is to a transfer substrate, as this connection is not intended to be permanent. Thereafter, the liftoff step 50, the second electrode deposition step 52, the poling step 54 and electric property test step 56, which correlate to steps 20, 22, 24 and 26 of FIG. 1, are performed.

The piezoelectric elements are then bonded to a final target substrate 58, in a procedure similar in design to step 18 of FIG. 1. Following bonding step 58, the transfer substrate is removed 60. Thereafter, the steps of inserting an insulative filler 62, bonding to the second final target substrate 64 and removal of the carrier plate 66, are performed similar to steps 28, 30 and 32 of FIG. 1. When bonding to a final target substrate, a thin high strength bonding layer is used to minimize or avoid undesirable mechanical damping or absorption of the bonding layer. This bonding will, however, also permit maintaining of electrical contact between the metal electrodes on the piezoelectric elements and the final target substrates or a conductive surface of the final target substrates.

Employing the process of FIG. 2, only fully tested thick film elements and arrays will be bonded to final target substrates, thus avoiding yield loss of the piezoelectric tape.

The processes of FIGS. 1 and 2 are appropriate for the production of a flexible piezoelectric ceramic tape in high volume, high usable yields, i.e. greater than 60 percent and more preferably over 90 percent, and still yet more preferably greater than 98 percent.

With attention to FIG. 3, which illustrates steps 12 and 42 in greater detail, piezoelectric ceramic elements 72 are deposited on an appropriate substrate 74, and then sintered at 1100 to 1350° C. for densification. The depositing step may be achieved by a number of direct marking processes including screen printing, jet printing, ballistic aerosol marking (BAM) or acoustic ejection, among others. Using these techniques permits flexibility as to the type of piezoelectric element configurations and thicknesses. For example, when the piezoelectric elements are made by screen printing, the screen printing mask (mesh) can be designed to have various shapes or openings resulting in a variety of shapes for the piezoelectric elements, such as rectangular, square, circular, ring, among others. Using single or multiple printing processes, the thickness of the piezoelectric elements can be from 10 µm to millimeter scale. Use of these direct marking techniques also permits generation of very fine patterns and high density elements.

The substrate used in the processes of this application will have certain characteristics, due to the high temperatures involved and—as will be discussed in greater detail—the fact that the substrate is to be transparent for the liftoff process. Specifically, the substrate is to be transparent at the wavelengths of radiation beam emitted from the radiation source, and is to be inert at the sintering temperatures so as not to contaminate the piezoelectric materials. A particularly appropriate substrate is sapphire. Other potential substrate materials include transparent alumina ceramics, aluminum nitride, magnesium oxide, strontium titanate, among others. In one embodiment of the process, the substrate selected is transparent for an excimer laser operating at a wavelength of 308 nm, and does not have any requirement on its crystallographic orientation. It is preferable that the selected substrate material be reusable, which will provide an economic benefit to the process.

After fabrication of the elements has been completed, the process moves to step 14 (or 44), where the top surface of the piezoelectric elements are polished through a tape polishing process to remove any possible surface damage layer, such as due to lead deficiency. This step ensures the quality of the piezoelectric elements and homogenizes the thickness of piezoelectric elements. By having a homogenized thickness, each of the piezoelectric elements of an array will bond to the final target substrate or the transfer substrate even when a very thin epoxy bonding layer or a thin film intermetallic transient liquid phase bonding layer is used.

In one preferred embodiment, the tape polishing step is a dry tape polishing process that provides a planar flat polish out to the edge of the surfaces of the piezoelectric elements, which avoids a crowning effect on the individual elements. Compared to wet polishing processes, the dry tape polishing does not cause wearing of the edges of the piezoelectric elements, making it possible to fabricate high-quality, thickness and shape-identical piezoelectric elements. Once polishing has been completed, the surface is cleaned, in one instance by application of a cleaning substance.

After polishing and cleaning, the process moves to step 16 (or 46) where, as shown in FIG. 4A, metal electrodes 76 such as Cr/Ni or other appropriate materials, are deposited on the surface of the piezoelectric elements by techniques such as sputtering or evaporation with a shadow mask. The electrodes can also be deposited by one of the direct marking methods, such as screen printing, and sintered at suitable temperatures. Alternatively, when using a thin film intermetallic transient liquid phase bonding process, certain low/high melting-point metal thin film layers may be used as the electrodes for the piezoelectric elements, thus in some cases it is not necessary to deposit the extra electrode layer such as Cr/Ni. However, preferably the thin film intermetallic transient liquid phase bonding process is undertaken after metal electrode deposition, such as Cr/Ni deposition. While this process will be discussed in greater detail below, generally a thin film layer of high melting-point metal 78 (such as silver (Ag), gold (Au), Copper (Cu), Palladium (Pd)) and a thin film layer of low melting-point metal 79 (such as Indium (In), Tin (Sn)) may be deposited on the piezoelectric elements (or the substrate) and a thin layer of high melting-point metal (such as Ag, Au, Cu, Pd) may be deposited on the substrate (or the piezoelectric elements). These materials are then used to form a bond. Also a multilayer structure with alternating low melting-point metal/high melting-point metal thin film layers can be used.

Figure 5A:
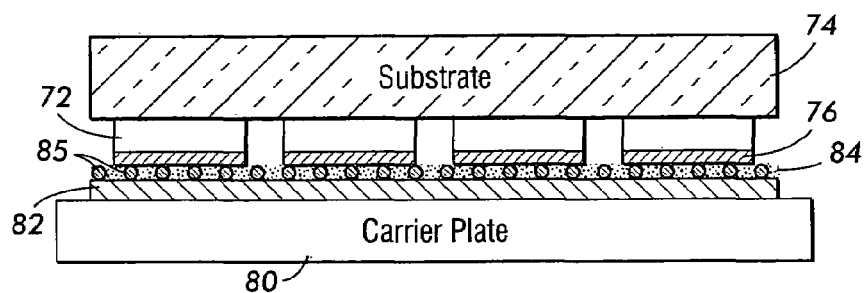
FIG. 5A illustrates an embodiment of a bonding of piezoelectric elements to a conductive final target using a thin, nonconductive epoxy bonding containing sub-µm (micrometer) conductive balls.

For some uses, such as when the final target substrate or system is not expensive, the piezoelectric elements are directly bonded to the final target substrate (step 18 of FIG. 1). For example, as depicted in FIG. 5A, the final target substrate 82 is a flexible and conductive material, such as a metal foil (thus it can also be used as common electrode). The final target substrate 82 could also be carried on a carrier plate 80 during the process. The placement of final target substrate 82 to carrier plate 80 may be an action where no bonding material is used between the two components. In alternative embodiments some type of removable adhesive may be used to ensure placement of the metal foil.

The bonding to piezoelectric elements 72 is accomplished by using a nonconductive epoxy layer 84 which can be as thin as less than 1 μm. The thin epoxy contains sub-μm conductive particles, which in one embodiment may be conductive balls (such as Au balls) 85 so the epoxy is conductive in the Z direction (the direction perpendicular to the surface of metal foil). Thus it can keep the electric contact between the surface electrode of the piezoelectric elements and the metal foil. The concentration of the conductive balls can be controlled in such a range that the cured thin epoxy is conductive in the Z direction but not conductive in the lateral directions, as done for the anisotropic conductive films. The shrinkage of the epoxy maintains contact between the surfaces and the balls in the Z direction.

Figure 5B:
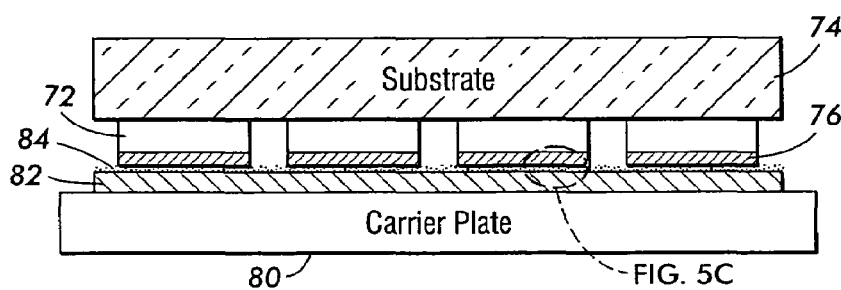
FIG. 5B shows a thin nonconductive epoxy bonding process.
Figure 5C:
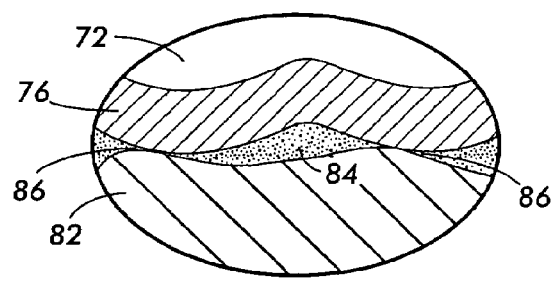
FIG. 5C is an enlarged view of a section of FIG. 5B.

In an alternative embodiment shown in FIGS. 5B and 5C, conductive balls 85 are removed, and bonding is accomplished using the nonconductive epoxy layer 84 alone. As shown in more detail by FIG. 5C, with controlled suitable surface roughness or asperity of the piezoelectric elements and/or the final target substrate, electrical contact is maintained via electrical contact points 86, formed when the surface of the electrode 84 and metal foil 82 are moved into contact.

Figure 5D:
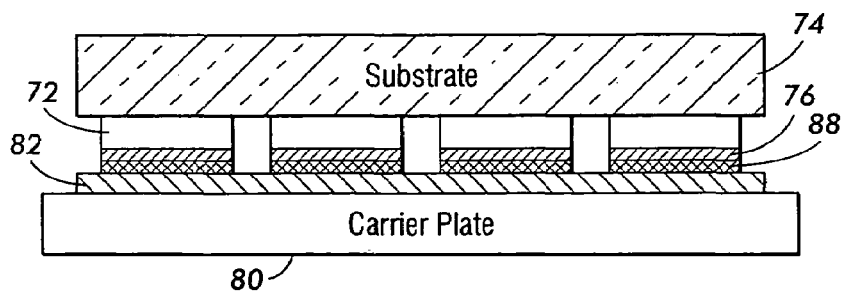
FIG. 5D illustrates a bonding of piezoelectric elements to a conductive final target substrate using thin film intermetallic transient liquid phase bonding.

In a further embodiment, bonding to the final target may be accomplished by using the previously mentioned thin film intermetallic transient liquid phase metal bonding, employing in one embodiment a high melting-point metal (such as Ag, Cu, Pd, Au, etc.)-low melting-point metal (such as In, Sn) intermetallic compound bonding layer or alloy 88, FIG. 5D.

More particularly, for thin film intermetallic transient liquid phase metal bonding, a high melting-point metal thin layer such as a Pd thin layer is deposited on the target substrate. Next the piezoelectric elements are moved into contact with the Pd thin layer and heated under pressure above the melting point of the low melting-point metal (In), e.g., about 200° C. By this operation the high melting-point metal/low melting-point metal/high melting-point metal combination such as the Pd/In/Pd layer (a high melting-point metal/low melting-point metal such as Pd/In layer was previously deposited on the piezoelectric elements as shown in FIG. 4B) will form the high melting-point metal-low melting-point metal intermetallic compound bonding layer or alloy 88. This compound or alloy may be a $PdIn_3$ alloy layer which is about 1 μm-thick, which acts to bond piezoelectric elements 72 and target substrate 82. Functionally, the low melting-point metal diffuses into the high melting-point metal to form the compound/alloy.

As the melting point of the formed intermetallic compound phase can be much higher than that of the low melting-point metal, the working temperature of the bonding layer can be much higher than the temperature used to form the bonding. For example, when Indium (In) is used as the low melting-point metal and Palladium (Pd) is used as the high melting-point metal, the bonding can be finished below or at 200° C. as the melting point of In is about 156° C. However, the working temperature of the formed intermetallic compound bonding layer, $PdIn_3$, can be well above 200° C. because the melting point of $PdIn_3$ is about 664° C. The thickness of the bonding layer could be from 1 to 10 μm, but a thinner bonding layer (e.g., about 1 μm) is expected for this purpose. Further, the amount of high and low melting-point metals can be controlled so they will be totally consumed to form the intermetallic bonding layer.

Alternatively, when the final target substrate is expensive, or the final target substrate is so large (to fabricate a very large piezoelectric tape) that the piezoelectric elements have to be fabricated on more than one substrate, bonding of the piezoelectric elements to the final target substrate is delayed. Incorporation of the steps in FIG. 2 minimizes yield loss of the final target substrate or the large area piezoelectric tape, which might otherwise occur due to piezoelectric elements fabrication failures. Therefore, the process of FIG. 2 temporarily bonds the piezoelectric elements to a transfer substrate in step 48, and then finishes piezoelectric elements production and testing. Only a fully tested piezoelectric thick film array of elements is then permanently bonded to the target substrate.

Figure 6A:
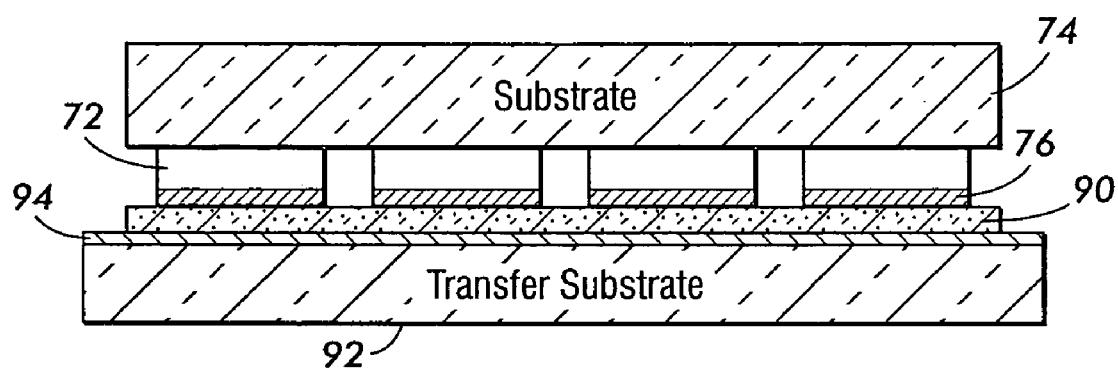
FIG. 6A depicts a bonding to a conductive transfer substrate using removable conductive tape bonding.
Figure 6B:
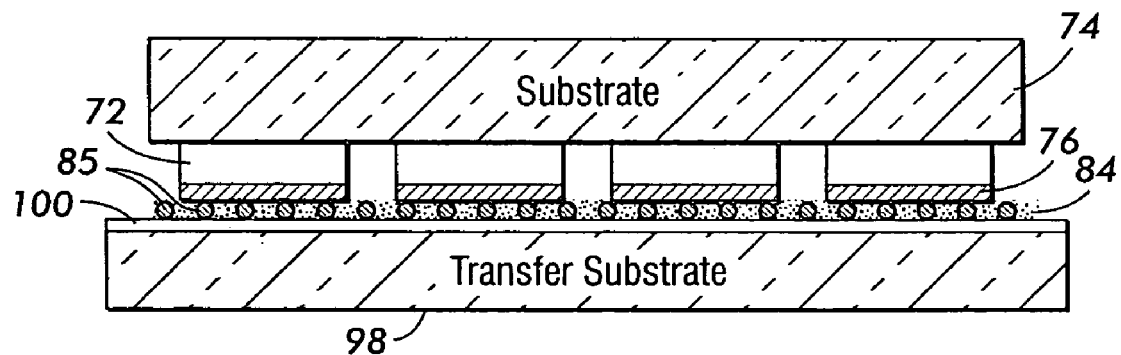
FIG. 6B illustrates a bonding of the piezoelectric elements to the transfer substrate which is an Indium-Tin-Oxide (ITO)-coated glass using thin, nonconductive epoxy bonding containing sub-µm conductive balls.

The temporary bonding process step 48 of FIG. 2, is illustrated by FIGS. 6A and 6B. In FIG. 6A, the bonding operation uses a removable conductive bonding epoxy, such as a removable conductive tape 90, including 9712, 9713 and 9719 conductive tape from 3M Corporation. The transfer substrate 92 can be a metallized glass with surface conductive layer 94, such as a metallization layer. In an alternative embodiment depicted in FIG. 6B, the bonding operation uses thin nonconductive epoxy 84 containing sub-μm conductive balls 85, to bond to a transfer substrate 98 such as a glass having an ITO coating 100.

Figure 7A:
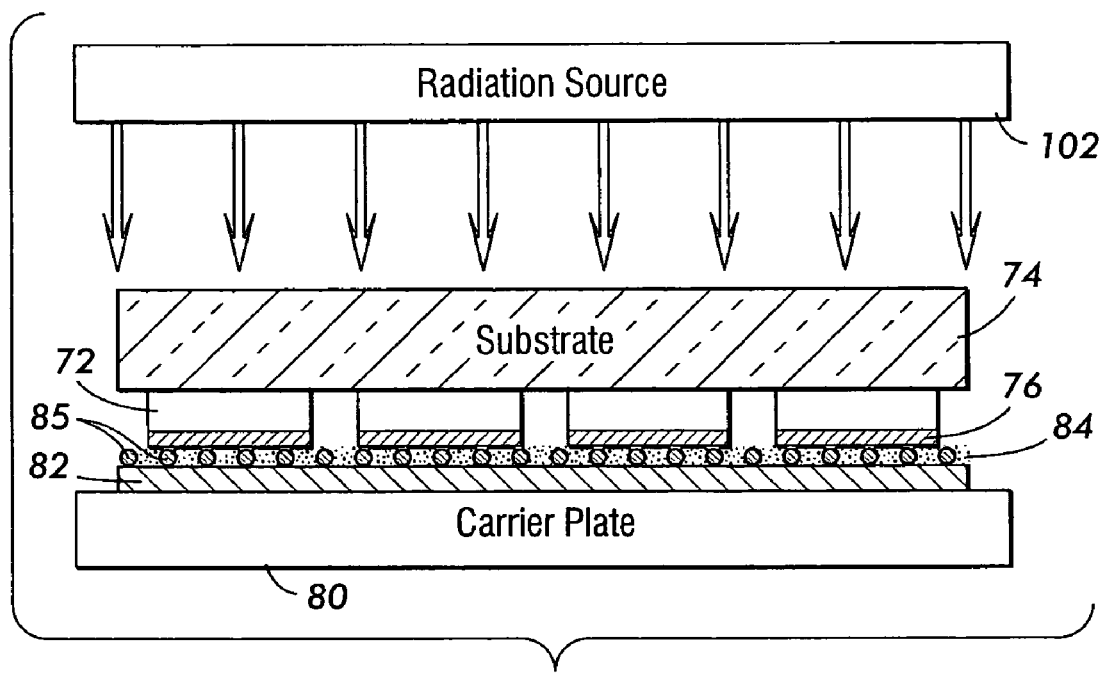
FIG. 7A illustrates radiation of a beam through the carrier substrate during a liftoff process.
Figure 7B:
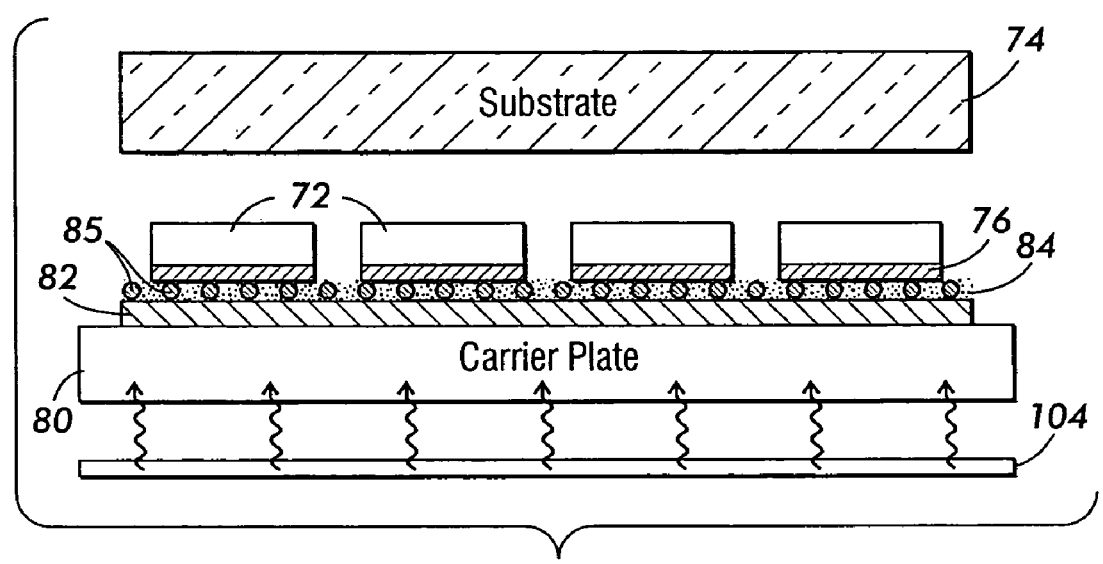
FIG. 7B depicts a heat transfer for the liftoff process.

Once the piezoelectric elements have been either permanently bonded to a final target substrate (step 18 of FIG. 1) or temporarily bonded to a transfer substrate (step 48 of FIG. 2), the next step is to release the piezoelectric elements 72 from substrate 74. The releasing of substrate 74 is accomplished by a liftoff operation as depicted in FIGS. 7A and 7B. The following description is based on the arrangement of FIG. 5A. However, it is applicable to all provided alternatives. Substrate 74 is first exposed to a radiation beam (such as a laser beam) from a radiation source (such as an excimer laser source) 102, having a wavelength at which the substrate 74 is substantially transparent. In this way a high percentage of the radiation beam passes through the substrate 74 to the interface of the substrate and elements 72 at the surface of the substrate. The energy at the interface acts to break down the physical attachment between these components. Following operation of the radiation exposure, and as shown in FIG. 7B, heat is applied by a heater 104. While the temperature provided by the heater will vary depending on the situation, in one embodiment a temperature of between 40 to 50° C. is sufficient to provide easy detachment of any remaining contacts to fully release the piezoelectric elements 72 from substrate 74. Desirably, the substrate is of a material that allows it to be re-used after a cleaning of its surface.

In one experiment performed by the inventors, the radiation source is an excimer laser source and the laser energy required to achieve separation by the present procedure has been measured at about one-half what is mentioned as needed in the Cheung et al. patent. This is considered in part due to the wavelength used in the experiment (e.g., 308 nm), and also that the piezoelectric elements were printed on substrates, therefore more weakly bound to the substrate compared to the epitaxially grown single crystal films used in the previous work by Cheung et al.

Exposure to the radiation source does raise the potential of damage to the surface of the piezoelectric elements, this potential damage should however be no more than to a thickness of about 0.1 μm. Since the thickness of the piezoelectric elements, in most embodiments, will be larger than 10 μm, the effect of the surface damage layer can be ignored. However, if otherwise necessary or when piezoelectric elements of less than 10 μm are formed by these processes, any surface damage layer can be removed by appropriate processes including ion milling or tape polishing. It is to be appreciated FIGS. 7A and 7B are simply used as examples, and the described liftoff process may take place using alternatively described arrangements. Also, for convenience FIGS. 7A and 7B correspond to the structure of FIG. 5A. However, the same types of procedures may be applied to FIGS. 5B, 5D, 6A, 6B or other relevant arrangements in accord with the present teachings.

Figure 8A:
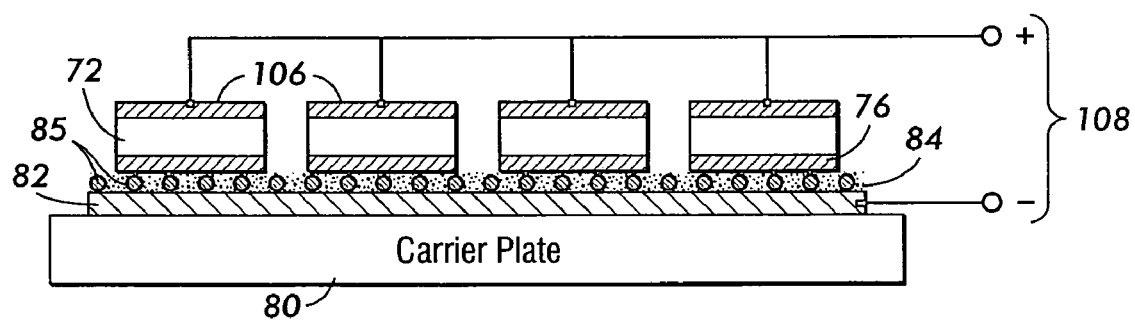
FIGS. 8A and 8B are alternative designs for bonding the elements array to a final target substrate or a transfer substrate.
Figure 8B:
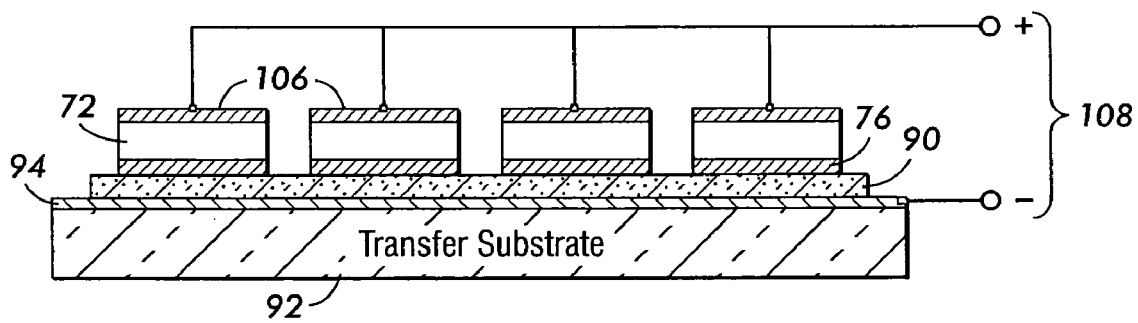

Next, as depicted in FIGS. 8A and 8B, second side surface electrodes 106, such as Cr/Ni, are deposited on the released surfaces of elements 72 with a shadow mask or by other appropriate method in accordance with step 22 of FIG. 1 or step 52 of FIG. 2. After second electrode deposition, the processes move to steps 24 and 54, respectively, where the piezoelectric elements 72 are poled under a voltage 108 sufficient, as known in the art, to obtain piezoelectric properties. After poling, the electric property, for example, the dielectric property, of the elements are measured (step 26 of FIG. 1; step 56 of FIG. 2) to identify if the piezoelectric elements meet expected quality criteria. FIG. 8A corresponds to the arrangements shown in FIG. 5A, and FIG. 8B corresponds to the arrangement of FIG. 6A, following release of the substrates.

For the case where the piezoelectric thick film array of elements is temporally bonded to a transfer substrate such as by the process of FIG. 2, steps 58 and 60 are undertaken. In the following these steps are implemented using selected ones of the alternative arrangements previously described. It is to be understood the present discussion is applicable for all disclosed alternative designs.

By use of temporary bonding, it is only after electric property measurement is made that the piezoelectric array is bonded to the final target substrate.

Step 58 of FIG. 2 may be accomplished in the same manner as bonding step 18 of FIG. 1. FIGS. 9A–9D, show alternative bonding methods, including a thin nonconductive epoxy bonding containing sub-μm conductive balls (FIG. 5A) and a thin film intermetallic transient liquid phase bonding (FIG. 5D). Still further, the process could employ the thin nonconductive epoxy bonding of FIGS. 5B and 5C. When this process is used, the surface roughness of the piezoelectric elements and/or the substrate is preferably in a range of about 0.5 to 5 μm, depending on the film thickness, the nature of the substrate, as well as the intended use. The second surface of the piezoelectric elements could be very smooth due to the smooth nature of the substrate surface. This means that, after liftoff, rough tape polishing, sandblasting or other methods may be needed to increase the surface roughness. It is to be understood the surface roughness will be a small fraction of the overall thickness of the piezoelectric element and/or substrate. The specific roughness being selected in accordance with a particular implementation.

If the thin film intermetallic transient liquid phase bonding is used, similar to previous steps, a high melting-point metal/low melting-point metal such as Pd/In is deposited on the second surface of the piezoelectric elements and a thin high melting-point metal such as Pd layer is deposited on the surface of the final target substrate. Deposition of the high melting-point/low melting-point metal layers on the piezoelectric elements can be done either after the poling and electric property test or before the poling and electric property test but after the electrode deposition.

It is to be appreciated that to make the flexible piezoelectric tape the final target substrate needs to be flexible and the final target substrate or the surface of the final target substrate needs to be conductive. Typically, the final target substrate could be a metal foil or a polymer tape with metallized surface layer. If appropriate, the final target substrate may also be put on rigid carrier plate 80, as shown in FIG. 5A, for easy carrying during the fabrication process. FIGS. 9A–9D are related to the process of FIG. 2, where the first bonding step is to a temporary connection, and the final target substrate 110 has a surface conductive layer 116.

Figure 9A:
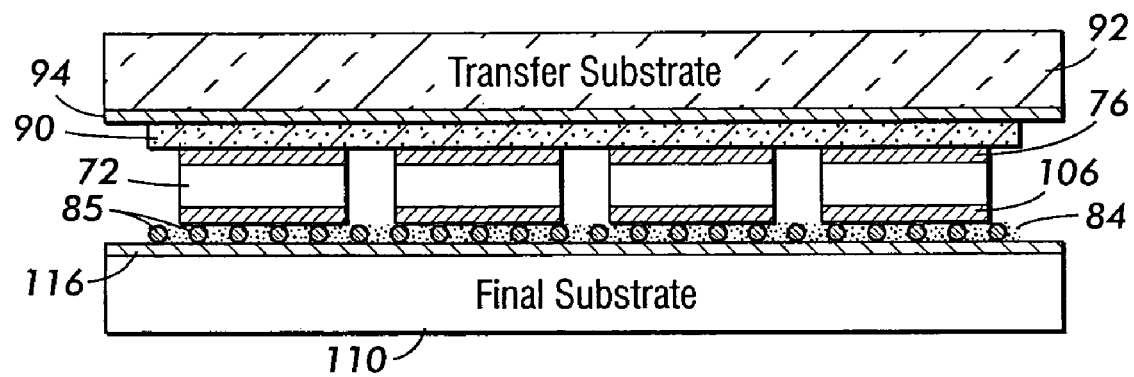
FIG. 9A illustrates bonding the piezoelectric elements array to a final target substrate using thin, nonconductive epoxy bonding containing sub-µm conductive balls, where the piezoelectric elements array is bonded to the transfer substrate using removable conductive tape bonding.

With more particular attention to FIG. 9A, to bond the piezoelectric elements 72 to final target substrate 110, nonconductive epoxy 84 containing sub-μm conductive balls 85 is interposed between a surface of the conductive layer 116 of the final target substrate 110 and piezoelectric elements 72 with electrodes 106. The opposite side surfaces of the piezoelectric elements 72 (i.e., having electrodes 76) are already temporarily bonded to the transfer substrate 92 (via conductor 94) through the use of a removable conductive tape 90.

Figure 9B:
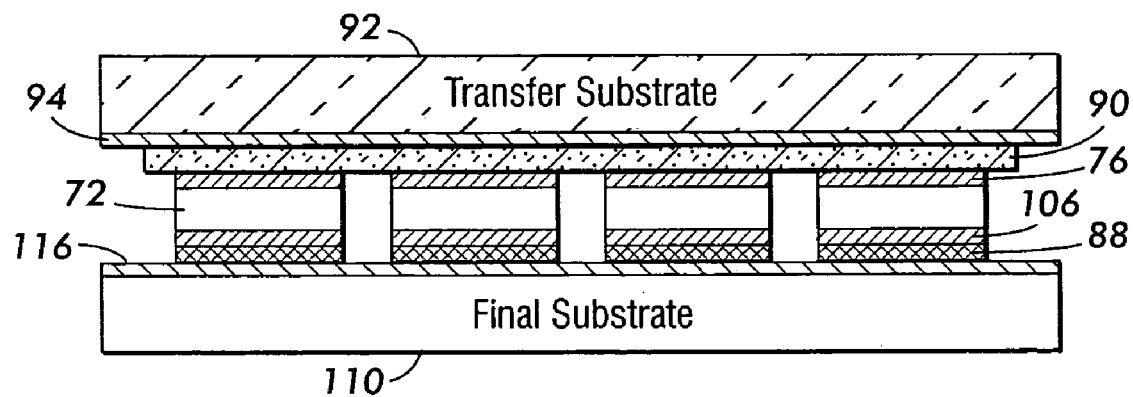
FIG. 9B is a bonding of the piezoelectric elements array to the final target substrate using thin film intermetallic transient liquid phase bonding, where the piezoelectric elements array is bonded to the transfer substrate using removable conductive tape bonding.

FIG. 9B illustrates an alternative bonding of the piezoelectric elements 72 to final target substrate 110 using thin film intermetallic transient liquid phase bonding 88, where the piezoelectric elements 72 are bonded to the transfer substrate 92 using removable conductive tape 90.

Figure 9C:
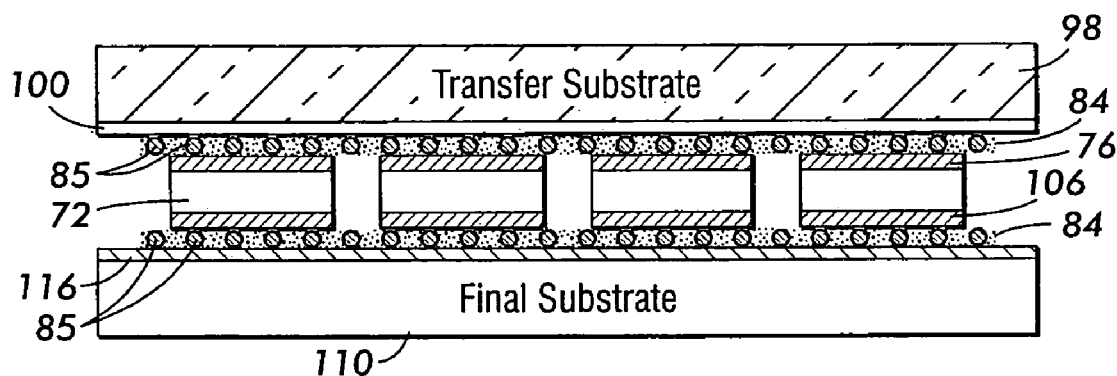
FIG. 9C is a bonding of the piezoelectric elements array to the final target substrate using thin, nonconductive epoxy bonding containing sub-µm conductive balls, where the piezoelectric elements array is bonded to an ITO-coated glass using the thin, nonconductive epoxy bonding containing sub-µm conductive balls.

The alternative bonding of FIG. 9C, shows the elements 72 bonded to the final target substrate 110 using thin nonconductive epoxy bonding 84 containing sub-μm conductive balls 85. In this design, elements 72 are bonded to an ITO coated 100 glass substrate 98 using the thin nonconductive epoxy 84 containing sub-μm conductive balls 85.

Figure 9D:
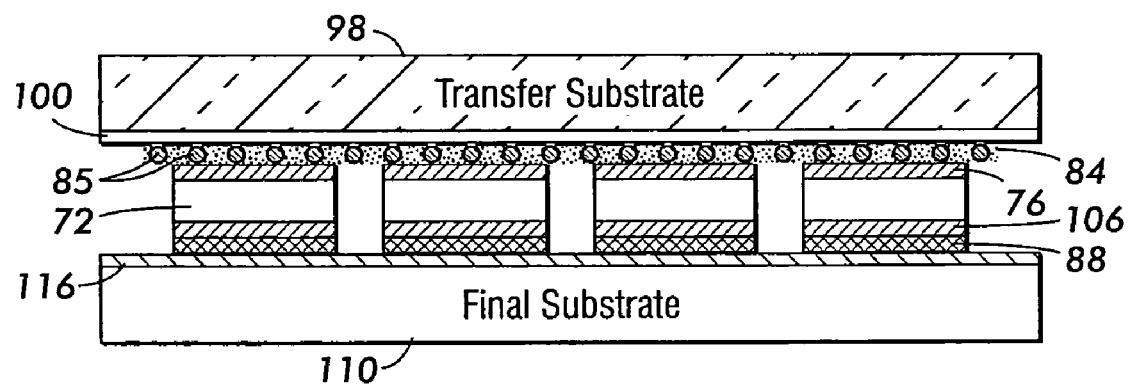
FIG. 9D depicts bonding the piezoelectric elements array to the final target substrate using thin film intermetallic transient liquid phase bonding, where the piezoelectric elements array is bonded to the ITO-coated glass using the thin, nonconductive epoxy bonding containing sub-µm conductive balls.

Depicted in FIG. 9D is an arrangement where the elements 72 are bonded to the final target substrate 110 using thin film intermetallic transient liquid phase bonding 88, where the piezoelectric elements 72 are bonded to ITO coated 100 glass 98 using the thin nonconductive epoxy 84 containing sub-μm conductive balls 85.

In some instances when fabricating a large piezoelectric tape, the final target substrate may be larger than the substrate available to deposit the piezoelectric elements. Alternatively, for economic reasons a relatively small substrate may be preferred to deposit the piezoelectric elements. In these situations, step 42 of FIG. 2 (or Step 12 of FIG. 1) may be accomplished by depositing the piezoelectric elements on several substrates. Thereafter processing steps 44 and 46 are performed. Since the piezoelectric elements will be on several substrates, step 48 will include bonding the piezoelectric elements to several transfer substrates. Then, following processing steps 50–56, in step 58 the several transfer substrates will be bonded to the same final target substrate. The foregoing process not only permit formation of large piezoelectric tapes and the use of small substrates, it also permits the attachment of different piezoelectric materials, such as soft PZT and hard PZT, or other functional ceramic materials, such as antiferroelectric materials, electrostrictive materials and magnetostrictive materials, on the same final target substrate. This means that the tape can contain different piezoelectric materials and/or other functional ceramic materials. For fabricating antiferroelectric elements and electrostrictive elements, the poling step (step 54) is not necessary.

Additionally, when bonded to the same final target substrate, if the distances between elements on one transfer substrate and another transfer substrate are sufficient, the thicknesses of the elements may be different from one transfer substrate to another, and a second flexible substrate (explained in details later) can still be bonded to the surface of all the elements. This means that the tape can contain elements with different thicknesses.

Figure 9E:
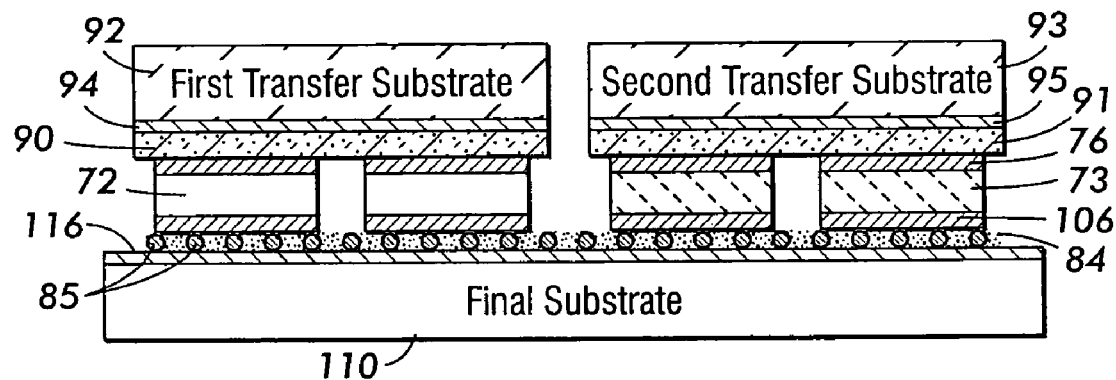
FIG. 9E depicts bonding the two elements arrays to a final target substrate using thin, nonconductive epoxy bonding containing sub-µm conductive balls, where the elements array is bonded to the transfer substrate using removable conductive tape bonding; the two elements arrays are deposited on two substrates and then transferred to two transfer substrates.
Figure 9F:
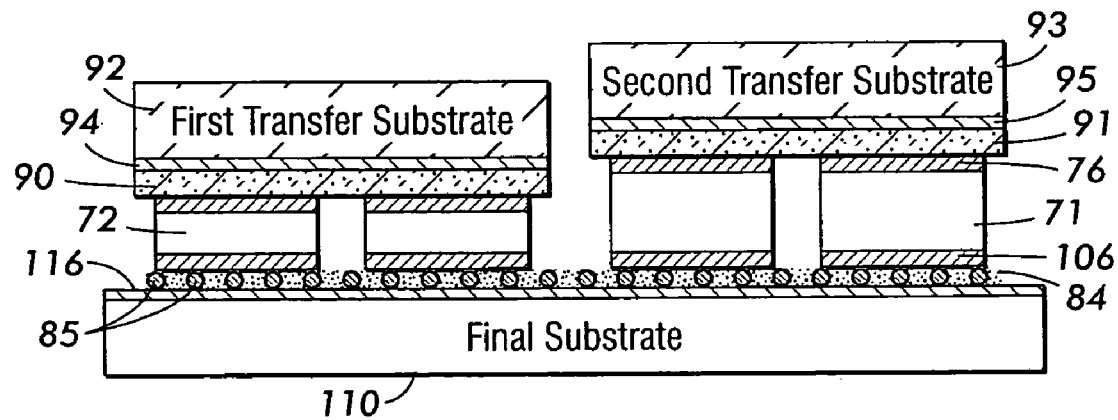
FIG. 9F depicts bonding the two elements arrays to a final target substrate using thin, nonconductive epoxy bonding containing sub-µm conductive balls, where the elements array is bonded to the transfer substrate using removable conductive tape bonding; the two elements arrays, with two different thicknesses for the elements from one array to the other, are deposited on two substrates and then transferred to two transfer substrate.

To illustrate the above concepts, FIG. 9E depicts two transfer substrates 92, and 93. Transfer substrate 92 has piezoelectric elements 72 bonded on it using removable conductive tape 90, and transfer substrate 93 has elements 73 (which may be another kind of piezoelectric material or other functional ceramic materials) bonded on it using removable conductive tape 91. The elements 72 and 73 are bonded to the same final target substrate 110 using the thin nonconductive epoxy bonding 84 containing sub-μm conductive balls 85. FIG. 9F depicts transfer substrates 92 and 93, where transfer substrate 92 has elements 72 bonded on it using removable conductive tape 90, and transfer substrate 93 has elements 71, which have thicknesses different from elements 72, bonded using removable conductive tape 91. Elements 72 and 71 are bonded to the same final target substrate using the thin nonconductive epoxy bonding 84 containing sub-μm conductive balls 85. The distance between elements 71 and 72 is large enough so the second flexible substrate can be bonded to all elements.

Figure 10A:
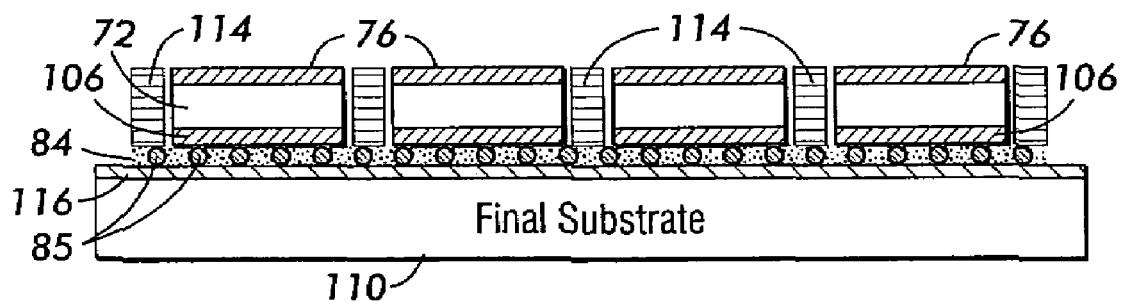
FIGS. 10A and 10B depict alternative embodiments of a partially constructed system, wherein filler is inserted.
Figure 10B:
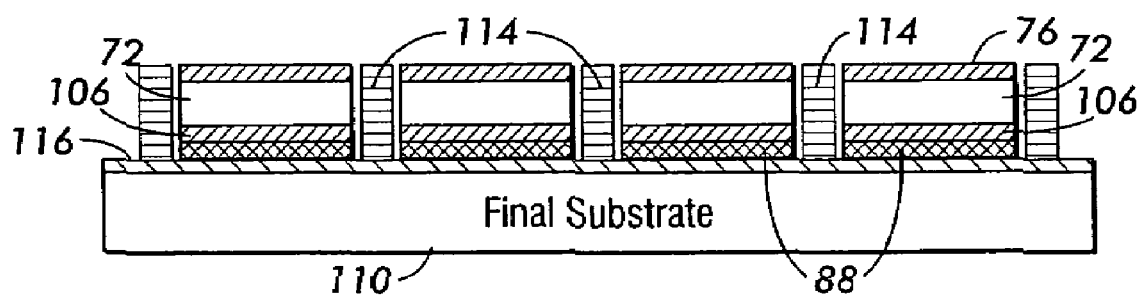

Once the final target substrate has been bonded to the elements, the process proceeds to step 60 and the transfer substrates (such as 92, 93) are removed, as shown in FIGS. 10A and 10B. For the case where the piezoelectric elements are bonded to the transfer substrate using removable conductive epoxy, such as tape, after permanent bonding to the final target is achieved, the tape and the transfer substrate can be easily peeled off from the piezoelectric elements. The present process makes it easy to take off the conductive tape. This is because the conductive tape uses filled acrylic, such as the 3M 9712, 9713 and 9719 conductive tapes, which lose most of their adhesion after being heated at a temperature of between 150 and 200° C. The time needed for application of the heat will depend upon the specific application. In some applications this level of heat may be applied during the process to bond the piezoelectric elements 72 to the final target substrate.

For the case where the piezoelectric elements 72 are bonded to the ITO coated glass using the thin nonconductive epoxy, the piezoelectric elements can be released from the ITO coated glass by using the liftoff operation in a manner similar as in steps 20 or 50 where the radiation source is a laser. This is possible as the epoxy will also absorb the laser light, thus the laser exposure will burn off the epoxy and release the piezoelectric elements from the glass substrate. As the melting point of epoxy is much lower than that of the metal and ITO electrodes, the laser exposure intensity may be controlled so it will only burn off the epoxy and not cause any damage on the metal and ITO electrodes.

Figure 11:
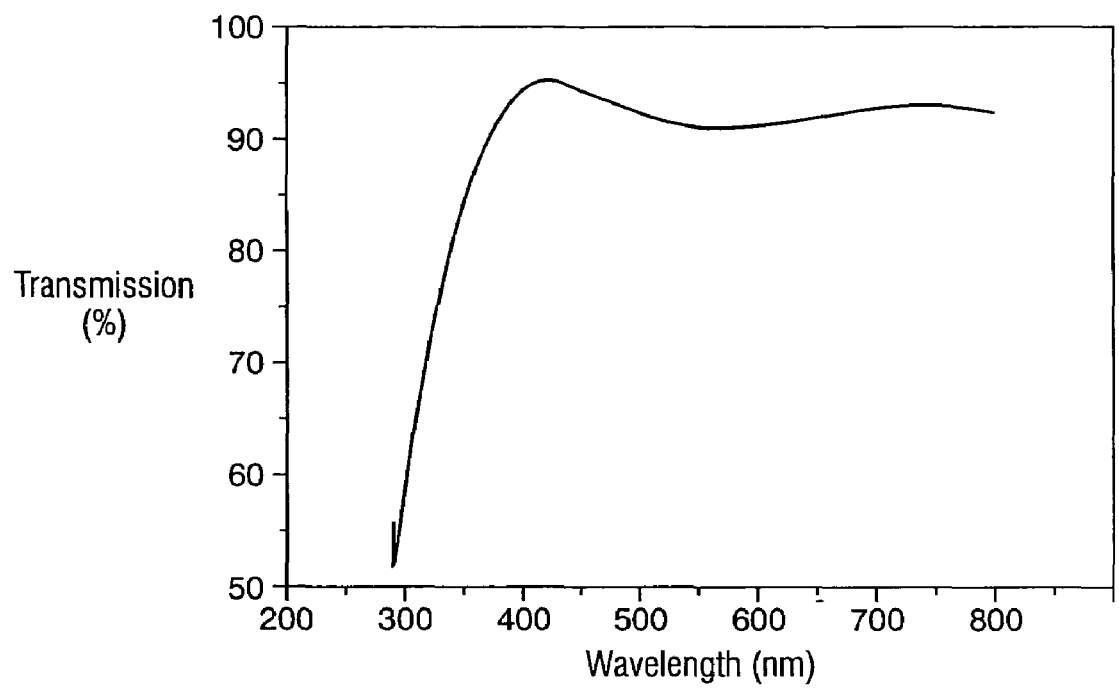
FIG. 11 is chart depicting transmission wavelength of a laser used in a process of the present application.

It should be noted that when using laser liftoff techniques to release the piezoelectric elements from ITO-coated glass, in one embodiment an excimer laser with relatively longer wavelength, such as Nd:YAG laser ($\lambda$=355 nm) and XeF ($\lambda$=351 nm) is to be used. This is because, as shown in FIG. 11, the transmission of light through ITO on glass will drop sharply around $\lambda$=300 nm, but around $\lambda$=350 nm the transmission can be about 80%. With such high transmission, the laser exposure can be controlled so that only the epoxy is destroyed and damage to the ITO and metal electrodes does not occur.

After removing the transfer carrier, solvent such as acetone or other appropriate substance may be used to clean off the residual of the conductive tape or the epoxy. Thereafter in step 28 (or 62), and as illustrated in FIGS. 10A and 10B, a filler material 114 is inserted between the piezoelectric elements 72. The filler 114 may be any appropriate insulative material including a punched polymer tape with openings slightly larger than the dimension of the piezoelectric elements 72.

Figure 12:
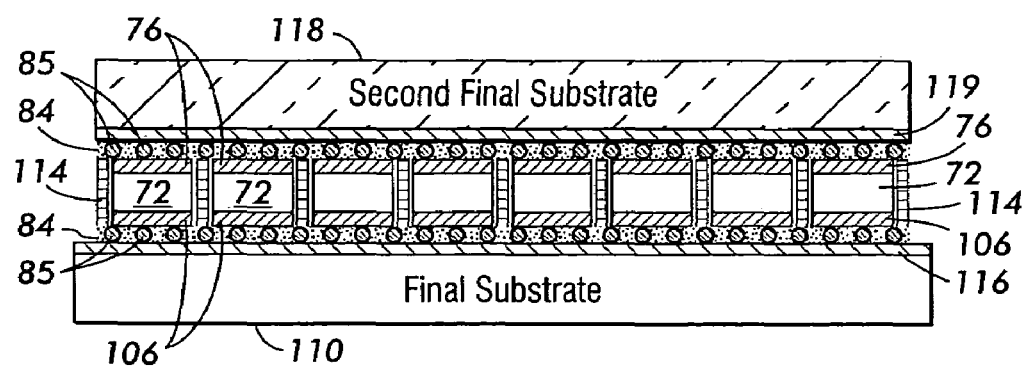
FIG. 12 depicts one embodiment wherein the second final target substrate is bonded to the piezoelectric elements.

Once the filler has been inserted, the process moves to step 30 (or 62) where, as depicted in FIG. 12, the second final target substrate 118 is bonded to the top of a second surface of the piezoelectric elements. Again the second final target substrate is flexible and the final target substrate or the surface of the final target substrate is conductive. Typically, the final target substrate could be a metal foil or a polymer tape with metallized surface layer. It is to be appreciated that FIG. 12 corresponds to the configuration of FIG. 10A, and the second final target substrate 118 has a surface conductive layer 119. However, the concept is also applicable to FIG. 10B, and other configurations which may be constructed according to the present application. In this embodiment, bonding is accomplished by thin nonconductive epoxy bonding 84 containing sub-μm conductive balls 85. However, it is to be appreciated other ones of the previously mentioned bonding techniques may also be used.

Lastly, the carrier plate 80 is removed (step 32, FIG. 1 or step 66, FIG. 2). It should be noticed that, while the carrier plate is not shown in FIGS. 9A–D, FIGS. 10A–B and FIG. 12, a rigid carrier plate (e.g., see FIGS. 5A–5B and 8A) may be located under the final target substrate to support the final target substrate and for carrying the final target substrate during the fabrication process.

Figure 13:
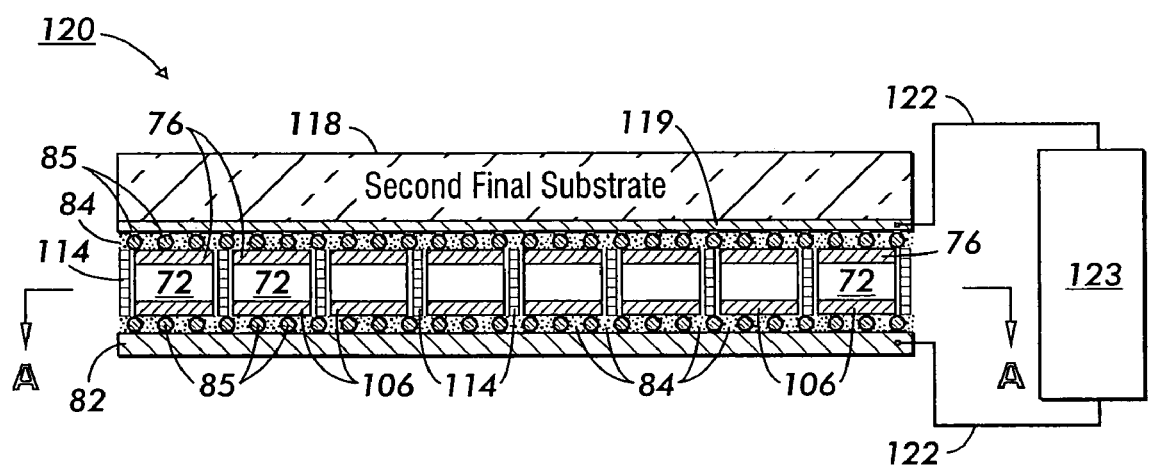
FIG. 13 is a cross section view for one embodiment of a completed piezoelectric tape according to the present application.
Figure 14:
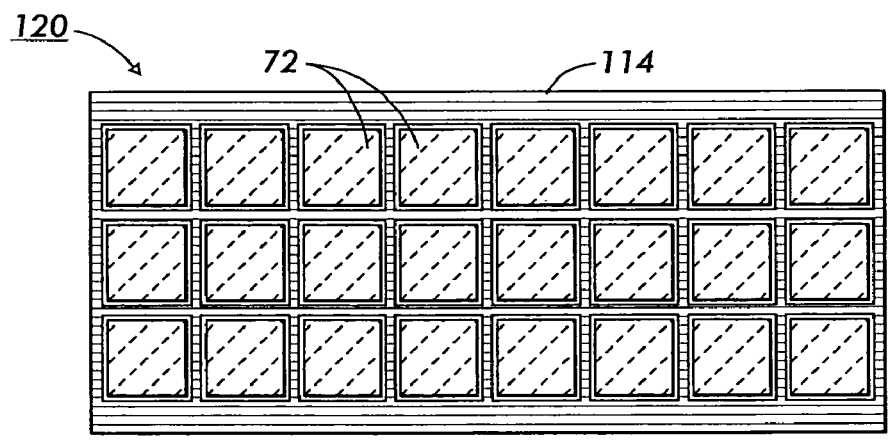
FIG. 14 is a sectional view along section line A—A of FIG. 13.

FIG. 13 shows one embodiment of a flexible tape 120 manufactured in accordance with the present application. FIG. 14 provides a A—A section view 120 of FIG. 13. In this configuration, a plurality of elements 72, such as piezoelectric elements, are sandwiched between final target substrate 82 and the second final target substrate 118. Substrates 82 and 118 are flexible and conductive or have a surface conductive layer. The procedure to make this tape is the same as the procedure to make the embodiment shown in FIG. 12 (therefore, final target substrate 110 with conductive surface 116 could just as easily have been used instead of substrates 82 or 118), but in this embodiment the final target substrate 82 is a conductive material or conductive layer, such as a metal foil, thus it does not have another conductive surface layer, and the second final target substrate 118 is an insulative material with a surface conducting layer 119, such as a metallized polymer tape.

For this design, the piezoelectric elements 72 are homogeneously distributed. It is to be appreciated that layers 82 and 118 are used as illustrative examples only, and other conductive material or material with surface conductive layer may also be used. Filler 114, such as punched mylar or teflon or other insulative material is positioned between the piezoelectric elements as insulation. The metallization layer 119 on polymer tape 118 is not patterned, thus all the piezoelectric elements 72 are connected together. Inclusion of electrical connectors 122 permit for the application of power and/or control signals. More particularly, known feedback or feed-forward control circuitry 123 is provided to control operation of the piezoelectric elements 72. Layers 82 and 118 are depicted as being bonded via the previously described thin nonconductive epoxy 84 bonding process containing sub-μm conductive balls 85. However, it is to be understood that any of the previously described bonding techniques may be employed.

The primary use of filler material 114 is to electrically isolate the (first) final substrate and the second final substrate or the surface conductive layers of these substrates from each other. However, it is to be understood insertion of the filler material is optional. For example, if the density of the elements is sufficiently high so that gaps between the elements are small enough that it is not possible to have an electric short circuit between the (first) final substrate and the second final substrate or their surface conductive layers even without any material filling the gaps between the elements, the insertion of filler material may be avoided. Also, filler material may not be used if the surface conductive layer of the substrate is patterned so there is no surface conductive layer in the areas which are not to be bonded to the piezoelectric elements.

Figure 15:
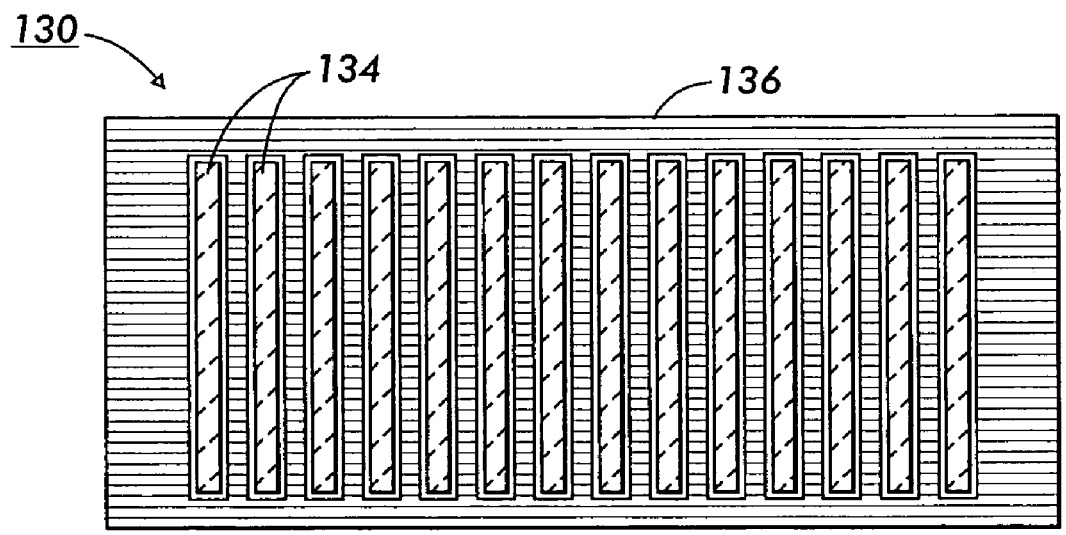
FIG. 15 is a sectional view at lines A—A, for another embodiment of a piezoelectric ceramic tape.

FIG. 15 is an A—A section view 130 for another embodiment of the tape of FIG. 13. This drawing emphasizes piezoelectric elements may be made as narrow and long strips 134, with the filler 136 configured to match this design. In this embodiment, the tape 130 can work as an active fiber composite, used in structures which require flexibility only along one direction, such as a cylindrical structure.

Figure 16:
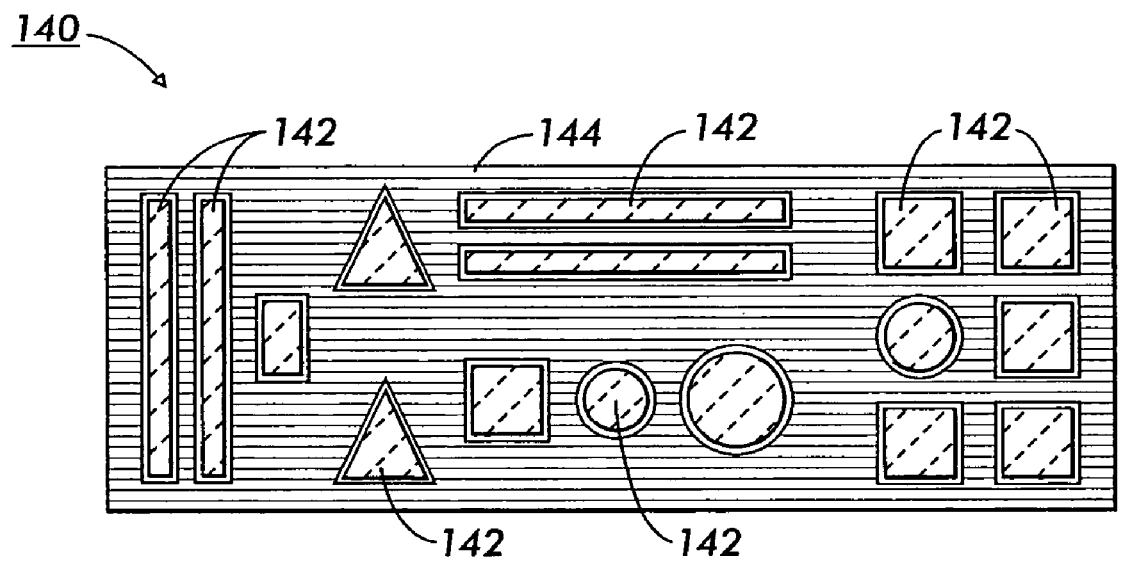
FIG. 16 is a further A—A sectional view of a further embodiment of a piezoelectric ceramic tape according to the present application.

FIG. 16 is a third embodiment of an A—A sectional view 140. This drawing shows that the density of piezoelectric elements in an area can be changed (i.e., the elements do not need to be evenly distributed in an area), and the piezoelectric elements may be formed in a variety of shapes 142. Thus the function of the piezoelectric tape can be locally adjusted. Filler 144 is distributed around and between the elements.

Figure 17:
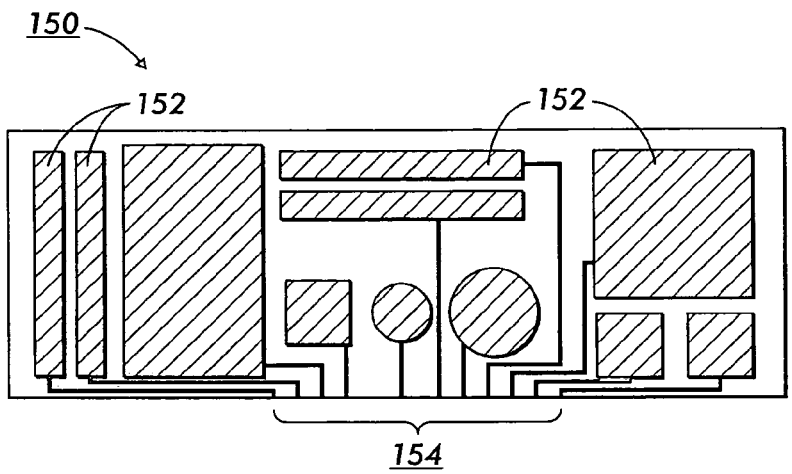
FIG. 17 depicts a polymer tape with a patterned metallization layer which may be implemented as a metal surface in accordance with the concepts of the present application.

FIG. 17 is a polymer tape 150 with a patterned metallization layer 152. Depending on the shape and distribution of the piezoelectric elements, and the design of outside circuits, the metallization layer can be patterned on the polymer tape 150 to connect the piezoelectric elements to external circuits, via circuit lines 154, individually or group by group, where the number of piezoelectric elements between groups can be different. With such circuit connection it is possible to simultaneously have some piezoelectric elements work as sensors, some as actuators, and some as transducers. Thus the piezoelectric tape itself is a detection/test panel or skin. For example, this purpose can be realized if the metallization layer 152 as shown in this figure is bonded to the piezoelectric elements shown in FIG. 16.

Figure 18A:
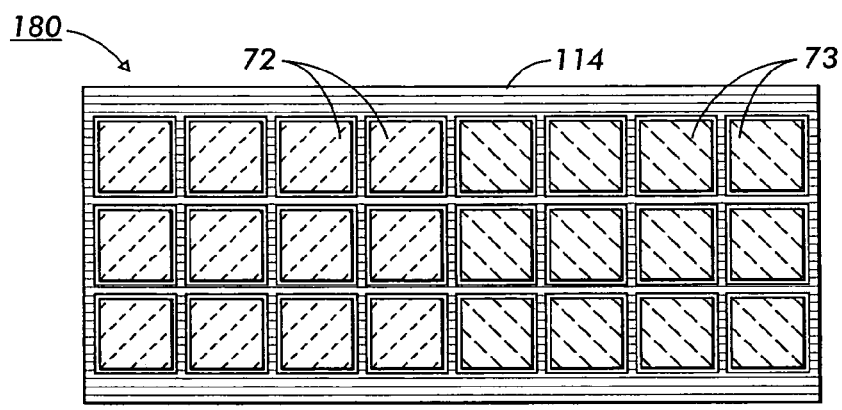
FIG. 18A is the A—A sectional view of the fourth embodiment of a piezoelectric ceramic tape.

FIG. 18A is a fourth embodiment of an A—A section view 180. This drawing emphasizes that in one tape it can have elements with different compositions (such as soft PZT and hard PZT) or some of the elements may be of piezoelectric material and other elements of other functional ceramic materials such as antiferroelectric material or electrostrictive material. For example, elements 72 are one kind of piezoelectric material and elements 73 are another kind of piezoelectric material or antiferroelectric or electrostrictive material. These different materials are made on different substrates and finally bonded to the same final target substrate, as previously described. These elements (made from different materials) can be connected together to a single outside circuit. However, more preferably they will be connected to the different outside circuits for different functions. For example, tape 190 can have a patterned metallization layer 192 shown in FIG. 18B. When this tape is used as the second final target substrate to bond the elements shown in FIG. 18A, all the elements 72 will work as a group and be connected to one outside circuit, and the elements 73, made from another kind of piezoelectric material or other functional ceramic material (such as antiferroelectric material or electrostrictive material) will work as another group and be connected to a separate outside circuit.

Figure 18B:
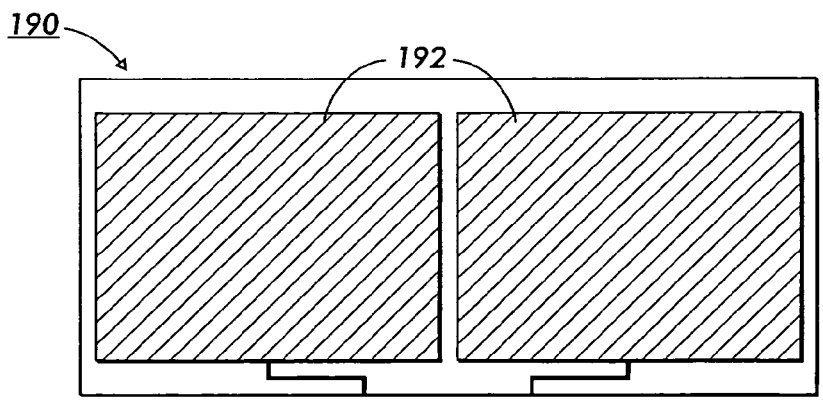
FIG. 18B depicts a polymer tape with a patterned metallization layer which could be used as the second final target substrate for the fourth embodiment.

FIG. 19 shows a further embodiment of a flexible tape 200 manufactured in accordance with the present application. In this configuration, a plurality of elements 72 and 71 are sandwiched between the final target substrate 82 and the second final target substrate 118. Substrates 82 and 118 are flexible and conductive or have a surface conductive layer. Shown in this embodiment the final target substrate 82 is a conductive material or conductive layer, such as a metal foil, thus it does not have another conductive surface layer. Final target substrate 118 is an insulative material with a surface conducting layer 119, such as a metallized polymer tape. However, unlike FIG. 13, the elements 72 and 71 in this embodiment have different thicknesses, and are fabricated on different substrates, but are finally bonded to the same final target substrate, as previously described. The distance between elements 72 and elements 71 is large enough so the second final target substrate (which is flexible) 118 can be bonded to both elements 72 and 71. Again while these elements with different thicknesses can be connected to a single external circuit together, more preferably they are connected to different external circuits for different functions. For example, when the polymer tape 190 shown in FIG. 18B is used as the second final target substrate to bond the elements shown in FIG. 19, elements 72 work as a group and are connected to a single external circuit, and the elements 71 are connected to a separate external circuit, in order to work as a group.

FIG. 20 is a double piezoelectric tape 160 made from two layers of single piezoelectric tape 162, 164 as configured, for example, in FIG. 13. In one embodiment, a double surface metallized polymer tape 166 is used to connect the two layers 162, 164. In this embodiment, metallization layers 167, 168, and 119 are individually numbered. While in this embodiment these metallization layers cover the whole surface of the polymer tape 166 and 118, depending on applications the metallization layers 167, 168, and 119 can be different materials, can be patterned and their patterned configurations can be different from one to another. Multilayer piezoelectric elements can also be made in accordance with the teachings of the present application.

The various embodiments of a ceramic tape as shown in FIGS. 13–20 are flexible tapes having the capability of selective operations, formed from the various piezoelectric elements provided as representative examples in these figures.

A further consideration in the construction of the tapes, is the placement of the piezoelectric elements in relation to the neutral plane of the tape. For a film or solid piece of material, the neutral plane is that location at which the sheer forces will move to zero during a bending operation. Particularly, it is the region inside the tape where the compressive force and the tensile force will cancel each other so as to eliminate sheer stress. Once the characteristics of the materials are known, such as the elastic modulus of the materials, it is possible to determine where a neutral plane will exist using well-known calculations. This information may be used in the present application to place the piezoelectric material relative to the plane to either increase or decrease the sensitivity of the piezoelectric elements, or to adjust the radius of curvature for the tape. Determinations on the placement of the piezoelectric element will be driven by the intended use of the tape. Particularly, placing the elements at the neutral plane will permit for an increase in the radius of curvature of the tape, thereby allowing the tape to be wrapped around a more tightly curved object. However, the tradeoff in providing this ability could cause a decrease in the sensitivity of readings that may be obtained.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A method of producing a detection/test tape comprising:
   depositing a material onto a surface of at least one first substrate to form a plurality of element structures, wherein the depositing step used to form the plurality of element structures includes direct marking methods;
   depositing electrodes on a surface of each of the plurality of element structures;
   bonding the element structures to a second substrate, the second substrate being conductive or having a conductive layer and the second substrate being carried on a carrier plate;
   removing the at least one first substrate from the element structures;
   depositing second side electrodes on a second surface of each of the plurality of element structures;
   bonding a second side of the element structures to a third substrate, the third substrate being conductive or having a conductive layer; and
   removing the carrier plate.

2. The method according to claim 1, wherein an insulative material is inserted in the gaps between the element structures to electrically isolate the two substrates or surface conductive layers of the two substrates used to bond the element structures.

3. The method according to claim 1, wherein the direct marking methods include at least one of screen printing, jet printing or acoustic printing.

4. A method of producing a detection/test tape comprising:
   depositing a material onto a surface of at least one first substrate to form a plurality of element structures;
   depositing electrodes on a surface of each of the plurality of element structures;
   bonding the element structures to a second substrate, the second substrate being conductive or having a conductive layer and the second substrate being carried on a carrier plate;
   removing the at least one first substrate from the element structures;
   depositing second side electrodes on a second surface of each of the plurality of element structures;
   bonding a second side of the element structures to a third substrate, the third substrate being conductive or having a conductive layer, wherein at least one of the second substrate or the third substrate is at least one of flexible or partially flexible; and
   removing the carrier plate.

5. The method according to claim 1, wherein the bonding step includes the use of at least one of nonconductive epoxy bonding containing conductive particles, a nonconductive epoxy alone, wherein electrical contact between the electrodes of the element structures and at least one of the second substrate or third substrate is maintained.

6. The method according to claim 1, wherein the bonding step includes a thin film metal bonding.

7. A method of producing a detection/test tape comprising:
   depositing a material onto a surface of at least one first substrate to form a plurality of element structures;
   depositing electrodes on a surface of each of the plurality of element structures;
   bonding the element structures to a second substrate, the second substrate being conductive or having a conductive layer and the second substrate being carried on carrier plate, wherein the step of bonding the element structures to the second substrate, includes the second substrate being a final target substrate, wherein the bond is intended to be permanent;
   removing the at least one first substrate from the element structures;
   depositing second side electrodes on a second surface of each of the plurality of element structures;
   bonding a second side of the element structures to a third substrate, the third substrate being conductive or having a conductive layer; and
   removing the carrier plate.

8. The method according to claim 1, wherein the step of bonding the element structures to at least one second substrate, includes the second substrate being a transfer substrate, wherein the bond is a temporary bond.

9. The method according to claim 8, further including,
   bonding element structures to a final target substrate, wherein the bond is intended to be permanent; and
   removing the at least one transfer substrate from the element structures.

10. The method according to claim 9, further including performing a property test on the element structures before bonding the element structures to a final target substrate.

11. A method of producing a detection/test tape comprising:
   depositing a material onto a surface of at least one first substrate to form a plurality of element structures, wherein the element structures are made from one of piezoelectric or other functional ceramic, including at least one of antiferroelectric material, electrostrictive material, and magnetostrictive materials;
   depositing electrodes on a surface of each of plurality of element structures;

bonding the element structures to a second substrate, the second substrate being conductive or having a conductive layer and the second substrate being carried on a carrier plate;

removing the at least one first substrate from the element structures;

depositing second side electrodes on a second surface of each of the plurality of element structures;

bonding a second side of the element structures to a third substrate, the third substrate being conductive or having conductive layer; and removing the carrier plate.

12. The method according to claim 1, wherein if more than one first substrate is used, the materials, shapes and thicknesses of the elements on these substrates are either the same or different.

13. A method of producing a detection/test tape comprising:

depositing a material onto a surface of at least one first substrate to form a plurality of element structures;

depositing electrodes on a surface of each of the plurality of element structures;

bonding the element structures to a second substrate, the second substrate being conductive or having a conductive layer and the second substrate being carried on a carrier plate;

removing the at least one first substrate from the element structures, further including, removing the at least one first substrate via a liftoff procedure using a radiation source;

depositing second side electrodes on a second surface of each of the plurality of element structures;

bonding a second side of the element structures to a third substrate, the third substrate being conductive or having a conductive layer; and removing the carrier plate.

14. A method of producing a detection/test tape comprising:

depositing a material onto a surface of at least one first substrate to form a plurality of element structures;

depositing electrodes on a surface of each of the plurality of element structures;

bonding the element structures to a second substrate, the second substrate being conductive or having a conductive layer and the second substrate being carried on a carrier plate;

removing the at least one first substrate from the element structures;

depositing second side electrodes on a second surface of each of the plurality of element structures;

bonding a second side of the element structures to a third substrate, the third substrate being conductive or having a conductive layer;

bonding a second plurality of element structures to another surface of the third substrate, the other surface of the third substrate being conductive or having a conductive layer;

removing the at least one first substrate from the second plurality of elements structures;

depositing electrodes on a second surface of each of the second plurality of element structures;

bonding a second side of the second plurality of element structures to a fourth substrate, the fourth substrate being conductive or having a conductive layer; and removing the carrier plate.

15. The method according to claims 13, wherein the at least one first substrate is transparent.

16. The method according to claim 13, wherein the radiation source is a laser.

17. The method according to claim 4, wherein an insulative material is inserted in the gaps between the element structures to electrically isolate the two substrates or surface conductive layers of the two substrates used to bond the element structures.

18. The method according to claim 4, wherein the bonding step includes the use of at least one of nonconductive epoxy bonding containing conductive particles, a nonconductive epoxy alone, wherein electrical contact between the electrodes of the element structures and at least one of the second substrate or third substrate is maintained.

19. The method according to claim 4, wherein the bonding step includes a thin film metal bonding.

* * * * *